United States Patent [19]

Burrows et al.

[11] Patent Number: 5,112,837
[45] Date of Patent: May 12, 1992

[54] QUINOLINE DERIVATIVES HAVING ANTI-TUMOR ACTIVITY

[75] Inventors: Kenneth D. Burrows, Warrington; Leslie R. Hughes, Macclesfield, both of United Kingdom; Peter Warner, Wilmington, Del.

[73] Assignee: Imperial Chemicals Industries PLC, London, England

[21] Appl. No.: 584,489

[22] Filed: Sep. 17, 1990

Related U.S. Application Data

[63] Continuation of Ser. No. 271,271, Nov. 15, 1988, abandoned.

[30] Foreign Application Priority Data

Nov. 26, 1987 [GB] United Kingdom ............... 8727737

[51] Int. Cl.$^5$ .................. A61K 31/47; C07D 215/00
[52] U.S. Cl. ................... 514/312; 514/311; 514/513; 514/314; 514/15; 514/16; 514/17; 514/18; 514/19; 546/153; 546/155; 546/162; 546/176; 546/161; 546/169; 546/180; 530/327; 530/328; 530/329; 530/330; 530/331; 530/332
[58] Field of Search ............ 546/153, 176, 162; 514/312, 314, 311, 313; 544/200

[56] References Cited

U.S. PATENT DOCUMENTS

| | | | |
|---|---|---|---|
| 4,447,608 | 5/1984 | Jones et al. | 544/287 |
| 4,447,608 | 5/1984 | Jones et al. | 544/287 |
| 4,547,509 | 10/1985 | Musser et al. | 514/311 |
| 4,564,616 | 1/1986 | Jones et al. | 544/287 |
| 4,621,088 | 11/1986 | LaRuelle et al. | 514/300 |
| 4,684,653 | 8/1987 | Taylor et al. | 544/260 |
| 4,746,659 | 5/1988 | DeGraw | 544/260 |
| 4,767,761 | 8/1988 | Rosawsky | 544/260 |
| 4,769,461 | 9/1988 | Musser | 546/176 |
| 4,814,454 | 3/1989 | Misra | 546/176 |
| 4,888,427 | 12/1989 | Bodor | 546/176 |
| 4,910,208 | 3/1990 | Misra | 514/312 |
| 4,946,207 | 2/1991 | Nair | 544/260 |
| 4,981,856 | 1/1991 | Hughes | 514/259 |
| 4,985,441 | 1/1991 | Hughes | 514/260 |
| 4,992,550 | 2/1991 | Hughes | 544/284 |

FOREIGN PATENT DOCUMENTS

0365763 2/1990 European Pat. Off. .

OTHER PUBLICATIONS

Burger, "Medicinal Chemistry" 2d. Ed., Interscience, New York, 1960, p. 42,497.

*Primary Examiner*—Donald G. Daus
*Attorney, Agent, or Firm*—Cushman, Darby & Cushman

[57] ABSTRACT

The invention relates to a quinoline of the formula:

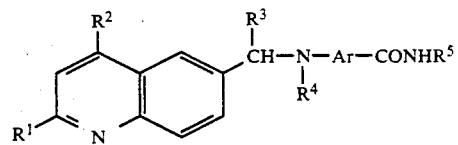

wherein each of $R^1$ and $R^2$, which may be the same or different, is hydrogen, halogeno, hydroxy, cyano, carbamoyl, nitro or amino, alkyl, alkoxy, alkylthio, alkylamino, dialkylamino or alkanoylamino each of up to 4 carbon atoms; or substituted alkyl or alkoxy each of up to 3 carbon atoms, provided that both $R^1$ and $R^2$ are not hydrogen; the quinoline ring may bear further substituents; $R^3$ is hydrogen or alkyl of up to 4 carbon atoms; $R^4$ is hydrogen, alkyl, alkenyl or alkynyl each of up to 4 carbon atoms or substituted alkyl of up to 3 carbon atoms; Ar is phenylene, naphthylene or heterocyclene which is unsubstituted or which bears one or more substituents; $R^5$ is such that $R^5$—$NH_2$ is an amino acid; or a pharmaceutically-acceptable salt or ester thereof. The compounds possess anti-tumor activity.

10 Claims, No Drawings

QUINOLINE DERIVATIVES HAVING ANTI-TUMOR ACTIVITY

This is a continuation of application Ser. No. 07/271,271, filed on Nov. 15, 1988, which was abandoned upon the filing hereof.

This invention relates to novel anti-tumour agents and more particularly it relates to quinoline derivatives which possess anti-tumour activity. The invention includes novel quinoline derivatives and processes for their manufacture; novel pharmaceutical compositions containing said quinoline derivatives and the use of said quinoline derivatives in the manufacture of novel medicaments for use in the production of an anti-tumour effect in a warm-blooded animal such as man.

One group of anti-tumour agents comprises the antimetabolites which are antagonists of folic acid, such as aminopterin and methotrexate. A newer compound of this type which showed considerable promise in clinical trials is known as CB3717 and is described and claimed in United Kingdom Patent Specification No. 2065653B. Despite its promising activity against human breast, ovarian and liver cancer, however, CB3717 shows symptoms of toxicity in humans, particularly in relation to the liver and kidney, [Calvert, Alison, Harland, Robinson, Jackman, Jones, Newell, Siddik, Whiltshaw, McElwain, Smith and Harrap, *J. Clin. Oncol.*, 1986, 4, 1245; Cantwell, Earnshaw and Harris, *Cancer Treatment Reports*, 1986, 70, 1335; Bassendine, Curtin, Loose, Harris and James, *J. Hepatol.*, 1987, 4, 39; Vest, Bork and Hasen, *Eur. J. Cancer Clin. Oncol.*, 1988, 24, 201; Cantwell, Macaulay, Harris, Kaye, Smith, Milsted and Calvert, *Eur. J. Cancer Clin. Oncol.*, 1988, 24, 733; Sessa, Zucchetti, Ginier, Willems, D'Incalci and Cavalli, *Eur. J. Cancer Clin. Oncol.*, 1988, 24, 769].

Compounds of the CB3717-type are believed to act as anti-tumour agents by inhibiting the enzyme thymidylate synthetase. The anti-tumour activity of CB3717 may be assessed in vitro by determining its inhibitory effect on that enzyme, and in cell cultures by its inhibitory effect on cancer cell lines such as the mouse leukemia cell lines L1210 and L5178Y TK-/- and the breast cancer cell line MCF-7.

Other compounds of the CB3717-type may therefore have their anti-tumour activity assessed and compared with that of CB3717, by their activity against, for example, the same enzyme and the same cancer cell lines.

We have now found that the quinoline derivatives of the present invention possess CB3717-type activity. Furthermore some of these compounds are more water-soluble than CB3717, which may be clinically important by increasing the rate of clearance of the compounds through the kidney thereby decreasing any symptoms of toxicity.

According to the invention there is provided a quinoline of the formula:

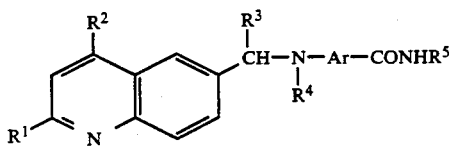

wherein each of $R^1$ and $R^2$, which may be the same or different, is hydrogen, halogeno, hydroxy, cyano, carbamoyl, nitro or amino; alkyl, alkoxy, alkylthio, alkylamino, dialkylamino or alkanoylamino each of up to 4 carbon atoms; or each of $R^1$ and $R^2$, which may be the same or different, is alkyl or alkoxy each of up to 3 carbon atoms which bears one or more substituents selected from halogen, hydroxy, amino, carbamoyl and alkoxy of up to 3 carbon atoms; provided that both $R^1$ and $R^2$ are not hydrogen; wherein the quinoline ring either bears no further substituent or bears one or two further substituents selected from halogeno, hydroxy, cyano, nitro and amino; alkyl and alkoxy each of up to 4 carbon atoms; and alkyl of up to 3 carbon atoms which bears one or more substituents selected from halogeno, hydroxy and alkoxy of up to 3 carbon atoms; wherein $R^3$ is hydrogen or alkyl of up to 4 carbon atoms; wherein $R^4$ is hydrogen, alkyl, alkenyl or alkynyl each of up to 4 carbon atoms or alkyl of up to 3 carbon atoms which bears one or more substituents selected from halogeno, hydroxy, cyano and alkanoyl of up to 4 carbon atoms; wherein Ar is phenylene, naphthylene or heterocyclene which is unsubstituted or which bears one or more substituents selected from halogeno, cyano, nitro, hydroxy and amino and alkyl, alkoxy, halogenoalkyl and alkanoylamino each of up to 4 carbon atoms; and wherein $R^5$ is such that $R^5$—$NH_2$ is an amino acid; or a pharmaceutically-acceptable salt or ester thereof.

In this specification the term "alkyl" includes both straight and branched alkyl groups but references to individual alkyl groups such as "propyl" are specific for the straight chain version only. An analogous convention applies to other generic terms.

It will be observed that a quinoline of the invention may possess one or more asymmetric carbon atoms and it can therefore exist in racemic and optically active forms. It is to be understood that this invention encompasses a racemic form of the quinoline and any optically-active form thereof which possesses anti-tumour activity, it being a matter of common general knowledge how a racemic compound may be separated into its optically-active forms.

Suitable values for the generic radicals referred to above include those set out below.

A suitable value for $R^1$ or $R^2$ when it is halogeno, or for a halogeno substituent which may be present as a further substituent on the quinoline ring or as a substituent on Ar is, for example, fluoro, chloro, bromo or iodo.

A suitable value for $R^1$, $R^2$, $R^3$ or $R^4$ when it is alkyl of up to 4 carbon atoms, or for an alkyl substituent of up to 4 carbon atoms which may be present as a further substituent on the quinoline ring or as a substituent on Ar is, for example, methyl, ethyl, propyl, isopropyl, butyl, isobutyl, sec-butyl or tert-butyl.

A suitable value for $R^1$ or $R^2$ when it is alkoxy of up to 4 carbon atoms, or for an alkoxy substituent of up to 4 carbon atoms which may be present as a further substituent on the quinoline ring or as a substituent on Ar is, for example, methoxy, ethoxy, propoxy, isopropoxy, butoxy, isobutoxy, sec-butoxy or tert-butoxy.

A suitable value for $R^1$ or $R^2$ when it is alkylthio of up to 4 carbon atoms is, for example, methylthio, ethylthio, propylthio, isopropylthio, butylthio, isobutylthio, sec-butylthio or tert-butylthio.

A suitable value for $R^1$ or $R^2$ when it is alkylamino or dialkylamino each of up to 4 carbon atoms is, for example, methylamino, ethylamino, propylamino, isopropylamino, butylamino, isobutylamino, sec-butylamino, tert-butylamino, dimethylamino, N-ethyl-N-methylamino or diethylamino.

A suitable value for $R^1$ or $R^2$ when it is alkanoylamino of up to 4 carbon atoms, or for an alkanoylamino substituent of up to 4 carbon atoms on Ar is, for example, acetamido, propionamido, butyrylamido or 2-methylpropionamido.

A suitable value for $R^1$ or $R^2$ or for a further substituent on the quinoline ring when it is alkyl of up to 3 carbon atoms which bears one or more substituents selected from halogeno, hydroxy and alkoxy of up to 3 carbon atoms is, for example, fluoromethyl, difluoromethyl, trifluoromethyl, 2-fluoroethyl, 3-fluoropropyl, chloromethyl, dichloromethyl, trichloromethyl, 2-chloroethyl, 3-chloropropyl, 2-bromoethyl, hydroxymethyl, 2-hydroxyethyl, 3-hydroxypropyl, methoxymethyl, 2-methoxyethyl, 3-methoxypropyl, ethoxymethyl or propoxymethyl.

A suitable value for $R^1$ or $R^2$ when it is substituted alkoxy of up to 3 carbon atoms is, for example, trifluoromethoxy, 2-fluoroethoxy, 2-hydroxyethoxy, 3-hydroxypropoxy, 2-methoxyethoxy, 3-methoxypropoxy, 2-ethoxyethoxy, 2-aminoethoxy, 3-aminopropoxy, carbamoylmethoxy or 2-carbamoylethoxy.

A suitable value for $R^1$ or $R^2$ when it is alkyl of up to 3 carbon atoms which bears one or more substituents selected from amino and carbamoyl is, for example, aminomethyl, 2-aminoethyl, 3-aminopropyl, carbamoylmethyl, 2-carbamoylethyl or 3-carbamoylpropyl.

Suitable positions for the further substituents which may be present on the quinoline ring are, for example the 3-, 5-, 7- and 8-positions. Mono-substitution in the 3- or 7-position is preferred.

A suitable value for $R^4$ when it is alkenyl or alkynyl each of up to 4 carbon atoms is, for example, prop-2-enyl, but-2-enyl, but-3-enyl, 2-methylprop-2-enyl, prop-2-ynyl, but-2-ynyl or but-3-ynyl.

A suitable value for $R^4$ when it is substituted alkyl of up to 3 carbon atoms is, for example, 2-fluoroethyl, 2-chloroethyl, 2-bromoethyl, 3-fluoropropyl, 3-chloropropyl, 2-hydroxyethyl, 3-hydroxypropyl, cyanomethyl, 2-cyanoethyl, 3-cyanopropyl, acetonyl, 2-acetylethyl or propionylmethyl.

A suitable value for Ar when it is heterocyclene is, for example, a 5-membered or 6-membered aromatic (that is, fully unsaturated) heterocyclene diradical which contains up to 2 heteroatoms selected from the group consisting of oxygen, nitrogen and sulphur, for example thienylene, pyridylene, pyrimidinylene, thiazolylene or oxazolylene.

A suitable value for a halogenoalkyl substituent of up to 4 carbon atoms which may be present on Ar is, for example, fluoromethyl, difluoromethyl or trifluoromethyl.

A suitable value for $R^5$ is such that $R^5$—$NH_2$ is a naturally-occurring amino-acid such as Glu, Ala, Phe, Ser, Asp, Met, Orn, Gly, Val, Leu or Ile.

Alternatively $R^5$ may be such that $R^5$—$NH_2$ is a poly-L-glutamic acid of the formula:

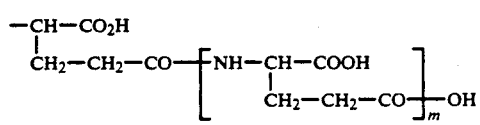

wherein m is an integer from 1 to 10.

Alternatively $R^5$ may be such that $R^5$—$NH_2$ is a D-amino-acid such as D-Val, D-Phe, D-Ser, D-Leu or D-Ala, or $R^5$—$NH_2$ is Abu, Ape, aIle, Phg or Tle.

In this specification the amino-acid residues are designated by their standard abbreviations (*Pure and Applied Chemistry*, 1974, 40, 317–331 and *European Journal of Biochemistry*, 1984, 138, 9–37). For the avoidance of doubt it is stated that:
amino-acid symbols denote the L-configuration unless otherwise indicated by D or DL appearing before the symbol and separated from it by a hyphen;
Orn designates ornithine i.e. 2,5-diaminopentanoic acid;
Abu designates 2-aminobutanoic acid;
Ape designates norvaline i.e. 2-aminopentanoic acid;
aIle designates L-alloisoleucine;
Phg designates L-2-phenylglycine i.e. (2S)-2-aminophenylacetic acid and
Tle designates L-tert-leucine i.e. L-α-(tert-butyl)glycine i.e. L-2-amino-3,3-dimethylbutanoic acid.

A suitable pharmaceutically-acceptable salt of a quinoline of the invention is, for example, an acid addition salt with, for example, an inorganic or organic acid, for example hydrochloric, hydrobromic, trifluoroacetic or maleic acid; or an alkali metal, for example sodium, alkaline earth metal, for example magnesium, or ammonium, for example tetra(2-hydroxyethyl)ammonium salt.

A suitable pharmaceutically-acceptable ester of a quinoline of the invention is, for example, an ester with an aliphatic alcohol of up to 4 carbon atoms, for example a methyl, ethyl or tert-butyl ester.

It is to be understood that when $R^5$ contains two carboxylic acid residues, that is, when it is derived from, for example, aspartic or glutamic acid, a salt or ester may be a mono-acid-mono-salt or ester or it may be a di-salt or ester.

A particular quinoline of the invention has the formula stated above
wherein $R^1$ is hydrogen, halogeno (especially chloro and bromo), carbamoyl, nitro or amino; alkyl (especially methyl, ethyl and isopropyl), alkoxy (especially methoxy and ethoxy), alkylthio (especially methylthio and ethylthio) or alkanoylamino (especially acetamido and propionamido) each of up to 4 carbon atoms; alkyl (especially methyl and ethyl) of up to 3 carbon atoms which bears one or more substituents selected from halogeno (especially fluoro), hydroxy, amino and carbamoyl; or alkoxy (especially ethoxy) of up to 3 carbon atoms which bears one or more substituents selected from hydroxy, amino and alkoxy (especially methoxy) of up to 3 carbon atoms;

wherein $R^2$ is hydrogen, halogeno (especially chloro and bromo), hydroxy, cyano or nitro; alkyl (especially methyl and ethyl), alkoxy (especially methoxy and ethoxy) or alkylthio (especially methylthio and ethylthio) each of up to 4 carbon atoms; alkyl (especially methyl and ethyl) of up to 3 carbon atoms which bears one or more substituents selected from alkoxy (especially methoxy and ethoxy) of up to 3 carbon atoms, amino and carbamoyl; or alkoxy (especially ethoxy) of up to 3 carbon atoms which bears one or more substituents selected from amino and carbamoyl; provided that both $R^1$ and $R^2$ are not hydrogen;

wherein the quinoline ring either bears no further substituent or bears one or two further substituents selected from halogeno (especially fluoro, chloro and bromo), hydroxy, cyano, nitro and amino; alkyl (especially methyl and ethyl) and alkoxy (especially methoxy and ethoxy) each of up to 4 carbon atoms; and alkyl (especially methyl and ethyl) of up to 3 carbon atoms which bears one or more substituents selected from halogeno (especially fluoro and chloro) and hydroxy (especially in the 3- or 7-position or in both the 3- and 7-positions);

wherein $R^3$ is hydrogen or alkyl (especially methyl) of up to 4 carbon atoms;

wherein $R^4$ is hydrogen, alkyl (especially methyl, ethyl and propyl), alkenyl (especially prop-2-enyl) or alkynyl (especially prop-2-ynyl) each of up to 4 carbon atoms or alkyl (especially ethyl) of up to 3 carbon atoms which bears one or more substituents selected from halogeno (especially fluoro, chloro and bromo), hydroxy and cyano;

wherein Ar is 1,4-phenylene, thien-2,5-diyl, pyrid-2,5-diyl, thiazol-2,5-diyl or oxazol-2,5-diyl which is unsubstituted or which bears one or more substituents selected from halogeno (especially fluoro, chloro and bromo), cyano, nitro, hydroxy and amino and alkyl (especially methyl and ethyl), alkoxy (especially methoxy and ethoxy), halogenoalkyl (especially trifluoromethyl) and alkanoylamino (especially acetamido) each of up to 4 carbon atoms; and wherein $R^5$ is such that $R^5$—$NH_2$ is Glu, Ala, Phe, Ser, Asp, Met, Orn, Gly, Val, Leu, Ile, Abu, Ape, aIle, Phg or Tle;

or a pharmaceutically-acceptable salt or ester thereof.

In each of the cases when Ar is pyrid-2,5-diyl, thiazol-2,5-diyl or oxazol-2,5-diyl it will be observed that two isomeric quinolines of the invention are possible with the heterocyclene group having the group —$CONHR^5$ in either the 2- or 5-position. It is to be understood that this invention encompasses any of these isomeric forms which possess anti-tumour activity.

A preferred quinoline of the invention has the formula stated above wherein $R^1$ is hydrogen, chloro, amino, methyl, ethyl, methoxy or trifluoromethyl;

wherein $R^2$ is hydrogen, chloro, bromo, hydroxy, cyano, methyl or methoxy; provided that both $R^1$ and $R^2$ are not hydrogen;

wherein the quinoline ring either bears no further substituent or bears one further chloro, bromo or methyl substituent (especially in the 3- or 7-position);

wherein $R^3$ is hydrogen or methyl;

wherein $R^4$ is hydrogen, methyl, ethyl, prop-2-enyl, prop-2-ynyl, 2-fluoroethyl, 2-bromoethyl, 2-hydroxyethyl or 3-hydroxypropyl;

wherein Ar is 1,4-phenylene which is unsubstituted or which bears one or two substituents selected from fluoro, chloro, hydroxy, amino and methyl (especially 2-fluoro-1,4-phenylene with the group —$CONHR^5$ in the 1-position), or Ar is thien-2,5-diyl, pyrid-2,5-diyl (with the group —$CONHR^5$ in the 2-position) or thiazol-2,5-diyl (with the group —$CONHR^5$ in the 2-position); and wherein $R^5$ is such that $R^5$—$NH_2$ is Glu, Val, Leu, Ile, Ape, aIle, Abu or Tle;

or a pharmaceutically-acceptable salt or ester thereof.

A further preferred quinoline of the invention has the formula stated above wherein $R^1$ is hydrogen, halogeno (especially chloro and bromo), carbamoyl or amino; alkyl (especially methyl and ethyl), alkoxy (especially methoxy and ethoxy) or alkanoylamino (especially acetamido and propionamido) each of up to 4 carbon atoms; alkyl (especially methyl and ethyl) of up to 3 carbon atoms which bears one or more substituents selected from halogeno (especially fluoro) and hydroxy; wherein $R^2$ is hydrogen, halogeno (especially chloro and bromo), hydroxy or cyano; alkyl (especially methyl and ethyl), alkoxy (especially methoxy and ethoxy) or alkylthio (especially methylthio and ethylthio) each of up to 4 carbon atoms; provided that both $R^1$ and $R^2$ are not hydrogen;

wherein the quinoline ring either bears no further substituent or bears one further substituent selected from halogeno (especially fluoro, chloro and bromo) and amino; alkyl (especially methyl and ethyl) of up to 4 carbon atoms; and alkyl (especially methyl and ethyl) of up to 3 carbon atoms which bears one hydroxy substituent (especially in the 3- or 7-position);

wherein $R^3$ is hydrogen or alkyl (especially methyl) of up to 4 carbon atoms;

wherein $R^4$ is hydrogen, alkyl (especially methyl, ethyl and propyl), alkenyl (especially prop-2-enyl) or alkynyl (especially prop-2-ynyl) each of up to 4 carbon atoms;

wherein Ar is 1,4-phenylene, thien-2,5-diyl or thiazol-2,5-diyl which is unsubstituted or which bears one or two halogeno substituents (especially fluoro, chloro and bromo); and wherein $R^5$ is such that $R^5$—$NH_2$ is Glu or Val;

or a pharmaceutically-acceptable salt or ester thereof.

A further preferred quinoline of the invention has the formula stated above wherein $R^1$ hydrogen, chloro, bromo, amino, methyl or trifluoromethyl;

wherein $R^2$ is hydrogen, chloro, bromo, methyl or methoxy; provided that both $R^1$ and $R^2$ are not hydrogen;

wherein the quinoline ring either bears no further substituent or bears one further fluoro, chloro, bromo, amino or methyl substituent (especially in the 3- or 7-position);

wherein $R^3$ is hydrogen;

wherein $R^4$ is hydrogen, methyl, ethyl, prop-2-enyl or prop-2-ynyl;

wherein Ar is 1,4-phenylene which is unsubstituted or which bears one or two fluoro substituents (especially 2-fluoro-1,4-phenylene with the group —$CONHR^5$ in the 1-position), or Ar is thien-2,5-diyl or thiazol-2,5-diyl (with the group —$CONHR^5$ in the 2-position); and wherein $R^5$ is such that $R^5$—$NH_2$ is Glu or Val; or a phramaceutically-acceptable salt or ester thereof.

An especially preferred quinoline of the invention has the formula stated above wherein $R^1$ is hydrogen, chloro, amino or methyl;

wherein $R^2$ is hydrogen, chloro, bromo or methyl; provided that both $R^1$ and $R^2$ are not hydrogen;

wherein the quinoline either bears no further substituent or bears one further amino substituent (especially in the 3-position);

wherein $R^3$ is hydrogen;

wherein $R^4$ is methyl, ethyl or prop-2-ynyl;

wherein Ar is 1,4-phenylene or 2-fluoro-1,4-phenylene (with the group —$CONHR^5$ in the 1-position); and wherein $R^5$ is such that $R^5$—$NH_2$ is Glu;

or a pharmaceutically-acceptable salt or ester thereof.

Specific particularly preferred quinolines of the invention form the group of compounds:

N-[4-[N-(2,4-dichloroquinolin-6-ylmethyl)-N-(prop-2-ynyl)amino]-2-fluorobenzoyl]-L-glutamic acid, N-[4-[N-(4-chloro-2-methylquinolin-6-ylmethyl)-N-(prop-2-ynyl)amino]-2-fluorobenzoyl]-L-glutamic acid, N-[4-[N-(4-bromo-2-methylquinolin-6-ylmethyl)-N-(prop-2-ynyl)amino]-2-fluorobenzoyl]-L-glutamic acid,
N-[4-[N-(4-chloro-2-methylquinolin-6-ylmethyl)-N-ethylamino]-2-fluorobenzoyl]-L-glutamic acid,
N-[4-[N-(2,4-dichloroquinolin-6-ylmethyl)-N-(prop-2-ynyl)amino]benzoyl]-L-glutamic acid,
N-[4-[N-(4-chloro-2,7-dimethylquinolin-6-ylmethyl)-N-(prop-2-ynyl)amino]benzoyl]-L-glutamic acid,
N-[4-[N-(4-chloro-2-trifluoromethylquinolin-6-ylmethyl)-N-(prop-2-ynyl)amino]benzoyl]-L-glutamic acid,
N-[4-[N-(2-chloro-4-methoxyquinolin-6-ylmethyl)-N-(prop-2-ynyl)amino]benzoyl]-L-glutamic acid,
N-[4-[N-(3-bromo-4-chloro-2-methylquinolin-6-ylmethyl)-N-(prop-2-ynyl)amino]benzoyl]-L-glutamic acid and
N-[4-[N-(4-chloro-2-methylquinolin-6-ylmethyl)-N-(prop-2-ynyl)amino]benzoyl]-L-valine.

Further specific particularly preferred quinolines of the invention form the group of compounds:
N-5-[N-(3-amino-4-chloroquinolin-6-ylmethyl)-N-methylamino]thiazole-2-carbonyl]-L-glutamic acid,
N-[4-[N-(2-amino-4-chloroquinolin-6-ylmethyl)-N-(prop-2-ynyl)amino]benzoyl]-L-glutamic acid,
N-[4-[N-(2-amino-4-methylquinolin-6-ylmethyl)-N-(prop-2-ynyl)amino]benzoyl]-L-glutamic acid,
N-[4-[N-(2-amino-4-chloroquinolin-6-ylmethyl)-N-(prop-2-ynyl)amino]-2-fluorobenzoyl]-L-glutamic acid,
N-[4-N-(3-amino-2-chloroquinolin-6-ylmethyl)-N-(prop-2-ynyl)amino]-2-fluorobenzoyl]-L-glutamic acid,
N-[4-[N-(3-amino-4-chloroquinolin-6-ylmethyl)-N-(prop-2-ynyl)amino]-2-fluorobenzoyl]-L-glutamic acid,
N-[5-[N-(2-amino-4-chloroquinolin-6-ylmethyl)-N-methylamino]thiazole-2-carbonyl]-L-glutamic acid,
N-[4-[N-(3-amino-4-chloroquinolin-6-ylmethyl)-N-(prop-2-ynyl)amino]benzoyl]-L-glutamic acid,
N-[5-[N-(4-chloro-2-methylquinolin-6-ylmethyl)-N-methylamino]thiazole-2-carbonyl]-L-glutamic acid and
N-[5-[N-(4-chloro-2-methylquinolin-6-ylmethyl)-N-methyl]amino]-2-thenoyl]-L-glutamic acid.

A quinoline of the invention may be prepared by any process known to be applicable for the preparation of chemically-related compounds.

A preferred process for the manufacture of a quinoline of the invention comprises the reaction of a compound of the formula:

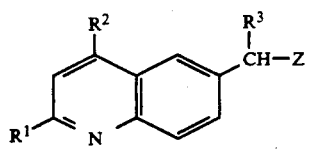

with a compound of the formula:

and within these compounds $R^1$, $R^2$, $R^3$, $R^4$, $R^5$ and Ar have the meanings stated above, provided that any basic amino group, and any carboxy group, in $R^1$, $R^2$, $R^5$ or Ar, or in a further substituent on the quinoline ring, is protected by a conventional protecting group, and any hydroxy group in $R^1$, $R^2$, $R^4$, $R^5$ or Ar, or in a further substituent on the quinoline ring, may be protected by a conventional protecting group or alternatively any hydroxy group need not be protected; and Z is a displaceable group; whereafter any undesired protecting group in $R^1$, $R^2$, $R^4$, $R^5$ or Ar, or in a further substituent on the quinoline ring, is removed by conventional means.

A suitable protecting group for a hydroxy group is, for example, an esterifying group, for example an acetyl or benzoyl group, which may be removed by hydrolysis with a base, for example sodium hydroxide, or provided that $R^4$ does not contain an alkenyl or alkynyl group and that an alkenyl or alkynyl group does not form a futher substituent on the quinoline ring, the protecting group may be, for example, an α-arylalkyl group, for example a benzyl group, which may be removed by hydrogenation over a catalyst, for example palladium-on-charcoal.

A suitable alternative protecting group for a hydroxy group is, for example, an alkyl group, for example a tert-butyl group, which may be removed by treatment with an organic acid, for example trifluoroacetic acid, or it may be removed by treatment with an inorganic acid, for example hydrofluoric or hydrobromic acid; or for example a methyl or ethyl group, which may be removed by treatment with a Lewis acid, for example boron tribromide or boron tris(trifluoroacetate).

A suitable protecting group for a basic amino group may be, for example, an alkoxycarbonyl group, for example a tert-butoxycarbonyl group which may be removed by treatment with an organic acid, for example trifluoroacetic acid or with an inorganic acid, for example hydrofluoric or hydrobromic acid; or it may be, for example, a benzyloxycarbonyl group which may be removed by treatment with a Lewis acid, for example boron tris(trifluoroacetate), or provided that $R^4$ does not contain an alkenyl or alkynyl group and that an alkenyl or alkynyl group does not form a further substituent on the quinoline ring, the protecting group may be removed by hydrogenation over a catalyst, for example palladium-on-charcoal.

A suitable alternative protecting group for a primary amino group is, for example, a phthaloyl group which may be removed by treatment with an alkylamine, for example dimethylaminopropylamine or with hydrazine.

A suitable protecting group for a carboxy group may be an esterifying group, for example a methyl or an ethyl group which may be removed by hydrolysis with a base, for example sodium hydroxide; or, for example a tert-butyl group which may be removed by treatment with an organic acid, for example trifluoroacetic acid.

Z may be, for example, a halogeno or sulphonyloxy group, for example a chloro, bromo, methanesulphonyloxy or toluene-p-sulphonyloxy group.

The protecting groups for the various carboxy groups in $R^5$ may be esterifying groups such as permit the product after removal of any undesired protecting groups in $R^1$, $R^2$, $R^4$, $R^5$ and Ar and of any protecting group on a further substituent on the quinoline ring to fall within the definition of a quinoline of the invention. In such instance the carboxy protecting groups in $R^5$ may be removed or they may be retained. Alternatively a different protecting group may be used which will be removed.

A further preferred process for the manufacture of a quinoline of the invention comprises the reaction of an acid of the formula:

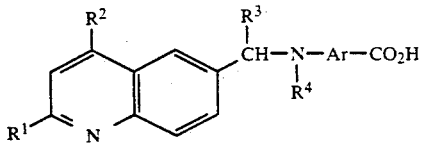

or a reactive derivative thereof, with a compound of the formula $R^5-NH_2$ and within these compounds $R^1$, $R^2$, $R^3$, $R^4$, $R^5$ and Ar have the meanings stated above, provided that any basic amino group, and any carboxy group in $R^1$, $R^2$, $R^5$ or Ar, or in a further substituent on the quinoline ring, is protected by a conventional protecting group as stated above, and any hydroxy group in $R^1$, $R^2$, $R^4$, $R^5$ or Ar, or in a further substituent on the quinoline ring, may be protected by a conventional protecting group, as stated above, or alternatively any hydroxy group need not be protected; whereafter any undesired protecting group in $R^1$, $R^2$, $R^4$, $R^5$ or Ar, or in a further substituent on the quinoline ring, is removed by conventional means.

A suitable reactive derivative of an acid of the formula given above may be, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an acyl azide, for example an azide formed by the reaction of the acid and an azide such as diphenylphosphoryl azide; or the product of the reaction of the acid and a carbodiimide, for example dicyclohexylcarbodiimide.

The carboxylic acid used as starting material may be obtained by the reaction of a compound of the formula:

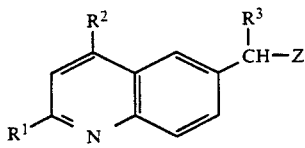

wherein $R^1$, $R^2$, $R^3$ and Z have the meanings state above, with a compound of the formula:

$$HNR^4-Ar-CO_2R^{10}$$

wherein $R^4$ and Ar have the meanings stated above and $R^{10}$ is a protecting group which can be removed to provide a carboxylic acid.

$R^{10}$ may be, for example, a methyl or an ethyl group which may be removed by hydrolysis with a base, for example sodium hydroxide or $R^{10}$ may be, for example, a tert-butyl group which may be removed by cleavage with an organic acid, for example trifluoroacetic acid.

The protecting group for the carboxy group in $R^{10}$ may be, for example, an esterifying group which can be removed while the protecting group for any basic amino group and any carboxy and hydroxy group in $R^1$, $R^2$, $R^4$ and Ar is retained.

As stated above a quinoline derivative of the present invention possesses anti-tumour activity. This activity may be assessed, for example, using one or more of the procedures set out below:

(a) An in vitro assay which determines the ability of a test compound to inhibit the enzyme thymidylate synthetase. Thymidylate synthetase was obtained in partially purified form from L1210 mouse leukaemia cells and utilised using the procedures described by Jackman et al. (*Cancer Res.*, 1986, 46, 2810);

(b) An assay which determines the ability of a test compound to inhibit the growth of the leukaemia cell line L1210 in cell culture. The test is similar to that described in UK Patent Specification No. 2065653B;

(c) An assay which determines the ability of a test compound to inhibit the growth of the human breast cancer cell line MCF-7 in cell culture. The test is similar to that described by Lippman et al. (*Cancer Res.*, 1975, 36, 4595); and (d) An assay which determines the ability of a test compound to inhibit the growth of the leukaemia cell line L5178Y TK-/- in vitro. The leukaemia cell line L5178Y TK-/- is deficient in the enzyme thymidine kinase which enzyme phosphorylates thymidine and thus operates to generate a pool of thymidylate when de novo synthesis of thymidylate is prevented by the presence of an effective amount of an inhibitor of thymidylate synthetase. The L5178Y TK-/-cell line is thereby more sensitive to the presence of an inhibitor of thymidylate synthetase. [L5178Y TK-/- was obtained by mutation of the parent L5178Y cell line which is described by, for example, Fischer et al., *Methods in Medical Research*, 1964, 10, 247]. The assay utilises a double layer soft-agar cloning technique similar to that described by Courtenay et al. (*British J. Cancer*, 1976, 34, 39). Each test compound is added at a range of concentrations to L5178Y TK-/- cells which have entered exponential growth phase in cell culture and the cells are incubated for 4 hours, harvested, washed with fresh culture medium and plated into soft-agar for clonogenic evaluation. After about 12 days colonies of cells are stained and counted.

A quinoline of the present inveniton may itself be active or it may be a pro-drug which is converted in vivo to an active compound.

Although the pharmacological properties in the quinolines of the invention vary with structural changes, in general quinolines of the invention possess activity in one or more of the above tests (a) to (d):
Test (a) IC$_{50}$ in the range, for example, 0.04–10 μM;
Test (b) IC$_{50}$ in the range, for example, 0.3–100 μM;
Test (c) IC$_{50}$ in the range, for example, 0.1–100 μM;
Test (d) The dose required to reduce the fraction of surviving cells to 10% of those treated lies in the range, for example, 5–100 μM.

In general those quinolines of the invention which are particularly preferred possess activity in one or more of the above tests (a) to (d):
Test (a) IC$_{50}$ in the range, for example, 0.04–0.4 μM;
Test (b) IC$_{50}$ in the range, for example, 0.3–20 μM;
Test (c) IC$_{50}$ in the range, for example, 0.1–5 μM;
Test (d) The dose required to reduce the fraction of surviving cells to 10% of those treated lies in the range, for example, 5–100 μM.

A quinoline of the invention may be administered to a warm-blooded animal, such as man, in the form of a pharmaceutical composition which comprises the quinoline in association with a pharmaceutically-acceptable diluent or carrier.

The composition may be in a form suitable for oral administration, as a tablet or capsule, or, especially, for parenteral injection, as a sterile solution, suspension or emulsion, or for topical administration, as an ointment or cream, or for rectal administration as a suppository.

The composition may contain, in addition to the quinoline of the invention, one or more other anti-tumour substances selected from, for example, mitotic inhibitors, for example vinblastine; alkylating agents, for example cis-platin, carboplatin and cyclophosphamide; other antimetabolites, for example 5-fluorouracil, cytosine arabinoside and hydroxyurea; intercalating antibiotics, for example adriamycin and bleomycin; enzymes, for example asparaginase; topoisomerase inhibitors, for example etoposide and biological response modifiers, for example interferon.

The quinoline will normally be administered to a warm-blooded animal, such as man, at a dose within the range 50–5000 mg per square meter body area of the animal i.e. approximately 1–100 mg per kilogram of animal weight, and this is considered to provide therapeutically-effective dose.

According to further feature of the present invention there is provided a method for producing an anti-tumour effect in a warm-blooded animal, such as man, in need of such treatment which comprises administering to said animal an effective amount of a quinoline of the present invention, or a pharmaceutically-acceptable salt or ester thereof. The invention also provides the use of a quinoline of the present invention, or a pharmaceutically-acceptable salt or ester thereof, in the manufacture of a novel medicament for use in the production of an anti-tumour effect in a warm blooded animal, such as man.

A quinoline of the present invention is expected to possess a wide range of anti-tumour activities. CB3717 showed promising activity against human breast, ovarian and liver cancer and consequently it is expected that a quinoline of the present invention will possess anti-tumour activity against these cancers. It is in addition expected that a quinoline of the present invention will possess anti-tumour activity against a range of leukaemias, lymphoid malignancies and solid tumours such as carcinomas and sarcomas. Such tumours require thymidine monophosphate as one of the essential nucleotides for the synthesis of cellular DNA. In the presence of an effective amount of a thymidylate synthetase inhibitor such as an effective amount of a quinoline of the present invention it is expected that tumour growth will be inhibited.

The invention is illustrated but not limited by the following examples.

The structures of all compounds of the invention were confirmed by proton magnetic resonance and mass spectroscopy and by elemental analysis. Proton magnetic resonance spectra were determined using a Jeol FX 90Q or a Bruker AM200 spectrometer operating at a field strength of 200 MHz. Chemical shifts are reported in parts per million downfield from tetramethylsilane as an internal standard ($\delta$ scale) and peak multiplicities are shown thus: s, singlet; d, doublet; d of d's, doublet of doublets; t, triplet, m, multiplet, Fast-atom bombardment (FAB) mass spectral data were obtained using a VG Analytical MS9 spectrometer and xenon gas and, where appropriate either positive ion data or negative ion data were collected.

Column chromatography was performed using Merck Art 9385 silica gel.

Intermediates were not generally fully characterised and purity ws assessed by one or more of thin layer chromatographic, infra-red (IR) and proton and magnetic resonance analysis.

EXAMPLE 1

A mixture of 6-bromomethyl-4-chloro-2-methylquinoline (4.67 g), diethyl N-[2-fluoro-4-(prop-2-ynyl)aminobenzoyl]-L-glutamate (6.56 g, prepared as described in UK Patent Specification No. 2188319A), 2,6-lutidine (2 ml) and dry dimethylformamide (80 ml) was stirred and heated to 70° C. under an atmosphere of argon for 18 hours. The mixture was cooled, poured into water (300 ml) and extracted with ethyl acetate (3×200 ml). The combined extracts were evaporated to give a dark oil which was purified by chromatography on a silica gel column using diethyl ether as eluent.

A mixture of the product so obtained (2.04 g), ethanol (40 ml) and aqueous N sodium hydroxide solution (21.6 ml) was stirred at laboratory temperature under an atmosphere of argon for 2.5 hours. The ethanol was evaporated and the resulting aqueous solution was filtered and acidified to pH 3 by adding 2N hydrochloric acid solution. The mixture was filtered and the solid residue was washed with water and diethyl ether and dried. There was thus obtained N-[4-[N-(4-chloro-2-methylquinolin-6-ylmethyl)-N-(prop-2-ynyl)amino]-2-fluorobenzoyl]-L-glutamic acid (containing 2 equivalents of water; 1.12 g), m.p. 115°–120° C.

NMR Spectrum: (CD$_3$SOCD$_3$) 2.0 (m, 2H, CH$_2$), 2.32 (t, J=7.5 Hz, 2H, CH$_2$CO$_2$H), 2.64 (s, 3H, CH$_3$), 3.28 (broad s, 1H, C≡CH), 4.37 (m, 1H, NHCH), 4.41 (d, J=1.5 Hz, 2H, CH$_2$C≡CH), 4.93 (s, 2H, CH$_2$N), 6.65 (d of d's, J=1.5 and 15 Hz, 1H, aromatic), 6.72 (d of d's, J=1.5 and 8 Hz, 1H, aromatic), 7.56 (t, J=9 Hz, 1H, aromatic), 7.67 (s, 1H, aromatic), 7.75 (d of d's, J=1.5 and 8 Hz, 1H, aromatic), 7.93 (m, 1H, NH), 7.97 (d, J=8 Hz, 1H, aromatic), 8.08 (d, J=1.5 Hz, 1H, aromatic).

Mass spectrum: (negative ion FAB) m/e 510 (P-1).

Elemental Analysis: Found C, 57.3; H, 4.6; N, 7.6; C$_{26}$H$_{23}$ClFN$_3$O$_5$. 2 H$_2$O requires C, 57.0; H, 5.0; N, 7.7%.

The quinoline used as starting material was obtained as follows:

A mixture of 2,6-dimethyl-4-quinoline (20 g, J. Org. Chem., 1946, 11, 741), N,N-dimethylaniline (27.97 g), phosphorus oxychloride (14.18 g) and toluene (200 ml) was heated at 90° C. for 3.5 hours. The resulting purple solution was poured into a mixture of ice and water (100 ml) and extracted with chloroform (4×100 ml). The combined extracts were evaporated and the resulting oil was purified by chromatography on a silica gel column using a 1:4 v/v mixture of ethyl acetate and petroleum ether (b.p. 60°–80° C.) as eluent. There was thus obtained 4-chloro-2,6-dimethylquinoline (18.9 g), m.p. 59°–61° C.

A mixture of 4-chloro-2,6-dimethylquinoline (6 g). N-bromosuccinimide (5.96 g), benzoyl peroxide (0.151 g) and carbon tetrachloride (120 ml) was heated at reflux for 3 hours during which time the mixture was illuminated by the light from a 250 Watt light bulb. The resulting mixture was filtered and the filtrate was evaporated to give an orange solid which was purified by chromatography on a silica gel column using a 1:4 v/v mixture of ethyl acetate and petroleum ether (b.p. 60°–80° C.) as eluent. There was thus obtained 6-bromomethyl-4-chloro-2-methylquinoline (4.7 g), m.p. 111°–113° C.

EXAMPLE 2

The process described in Example 1 was repeated using the appropriate 6-bromomethylquinoline and the appropriate dialkyl N-[4-aminobenzoyl]-L-glutamate as starting materials.

Unless it is otherwise stated the 6-bromomethyquinolines were prepared from the corresponding 6-methylquinolines using the bromination process described in the portion of Example 1 concerned with the preparation of starting materials. Unless it is otherwise stated diethyl N-[4-aminobenzoyl]-L-glutamates obtained as described in UK Patent Specification No. 2188319A were used.

There were thus obtained the compounds described in the following table, the structures of which were confirmed by proton magnetic resonance and mass spectroscopy and by elemental analysis.

c: 4-Chloro-6-methylquinoline was prepared using the method described in *J. Amer. Chem. Soc.*, 1948, 70, 1363.

d: 3-Bromo-4-chloro-2,6-dimethylquinoline used as a starting material for the preparation of 3-bromo-6-bromomethyl-4-chloro-2-methylquinoline was obtained as follows:

A mixture of 2,6-dimethyl-4-quinolone (5 g), N-bromosuccinimide (5.5 g), benzoyl peroxide (0.14 g) and carbon tetrachloride (75 ml) was heated at reflux for 2.5 hours during which time the mixture was illuminated by the light from a 250 Watt light bulb. The resulting mixture was filtered and the solid residue obtained was washed with methylene chloride. There was thus obtained 3-bromo-2,6-dimethyl-4-quinolone (7 g), m.p. 262°–264° C. A mixture of this product (7 g), N,N-dimethylaniline (7.3 ml), phosphorus oxychloride (2.1 ml) and toluene (100 ml) was heated at 90° C. for 3 hours.

TABLE I

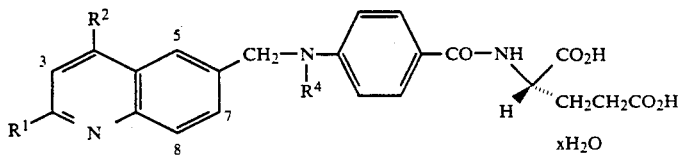

| Ex. 2 Compound No. | $R^1$ | $R^2$ | Other Subst. | $R^4$ | x | m.p. (°C.) |
| --- | --- | --- | --- | --- | --- | --- |
| 1[a] | Me | H | — | $CH_2C{\equiv}CH$ | 2 | 103–108 |
| 2[a] | Me | H | — | Et | 1.5 | 86–91 |
| 3[b] | Me | Me | — | $CH_2C{\equiv}CH$ | 2.6 | 118 |
| 4[b] | Me | Me | — | Et | 3.5 | 114 |
| 5[c] | H | Cl | — | Et | 1.5 | 114–120 |
| 6 | Me | Cl | — | $CH_2C{\equiv}CH$ | 1 | 130–135 |
| 7 | Me | Cl | — | Et | 1 | 128–130 |
| 8 | Me | Cl | — | Me | 1.5 | 180 |
| 9[d] | Me | Cl | 3-Br | $CH_2C{\equiv}CH$ | 2 | 149 |
| 10[d] | Me | Cl | 3-Br | Et | 1 | 117–123 |
| 11[d] | Me | Cl | 3-Br | Me | 0.5 | 129–134 |
| 12[e] | Me | Cl | 3-Cl | $CH_2C{\equiv}CH$ | 1 | 144–155 |
| 13[e] | Me | Cl | 3-Cl | Et | 1 | 136–142 |
| 14[f] | Me | Cl | 3-Me | $CH_2C{\equiv}CH$ | 1.5 | 133–140 |
| 15[g] | Me | Cl | 7-Me | $CH_2C{\equiv}CH$ | 3 | 190–194 |
| 16[h] | Et | Cl | — | $CH_2C{\equiv}CH$ | 1 | 104–110 |
| 17[i] | Me | Br | — | $CH_2C{\equiv}CH$ | 1.5 | 135–140 |
| 18[i] | Me | Br | — | Et | 1.5 | 165–170 |
| 19[j] | Me | CN | — | $CH_2C{\equiv}CH$ | 1 | 133–139 |
| 20[j] | Me | CN | — | Et | 1.5 | 125–129 |
| 21[k] | Me | OH | — | $CH_2C{\equiv}CH$ | 1.5 | 235 (decomp) |
| 22[k] | Me | OH | — | Et | 1 | 177–179 |
| 23[l] | $CF_3$ | Cl | — | $CH_2C{\equiv}CH$ | 0.5 | 90–94 |
| 24[l] | $CF_3$ | Cl | — | Et | 1 | 83–89 |
| 25[m] | Cl | Cl | — | $CH_2C{\equiv}CH$ | 0.5 | 110–117 |
| 26[n] | MeO | Cl | — | $CH_2C{\equiv}CH$ | 1 | 132–134 |
| 27[n] | Cl | MeO | — | $CH_2C{\equiv}CH$ | 2.2 | 85–90 |
| 28[o] | $CH_2OH$ | Cl | — | Et | 0.5 | 118–125 |
| 29[p] | Me | OMe | — | $CH_2C{\equiv}CH$ | 2 | 178–182 |
| 30[q] | Cl | Me | — | Me | 1 | 135–140 |
| 31 | Cl | Me | — | $CH_2C{\equiv}CH$ | 1 | 120–126 |
| 32[r] | Me | SMe | — | $CH_2C{\equiv}CH$ | 2 | 105–112 |
| 33[s] | $CONH_2$ | Cl | — | $CH_2C{\equiv}CH$ | 0.5 | 140–145 |
| 34[t] | Me | Cl | 8-F | $CH_2C{\equiv}CH$ | 0.8 | 116–124 |
| 35[u] | $CH_2F$ | Cl | — | $CH_2C{\equiv}CH$ | 2 | 97–106 |
| 36[v,w] | $NH_2$ | Me | — | $CH_2C{\equiv}CH$ | 1.3 | 205–210 |
| 37[x] | Br | Me | — | $CH_2C{\equiv}CH$ | 1.5 | 115–118 |
| 38[y] | Cl | H | — | Me | 0.5 | 115–118 |
| 39[y] | Cl | H | — | $CH_2C{\equiv}CH$ | 1.1 | 114–120 |
| 40[z] | Cl | H | 3-Cl | $CH_2C{\equiv}CH$ | 1.5 | 109–111 | a: 2,6-Dimethylquinoline was obtained from a commercial source.

b: 2,4,6-Trimethylquinoline was obtained from a commercial source.

The resulting solution was poured into a mixture of ice and water (150 ml) and chloroform (150 ml) was added. The two phase mixture was filtered, the layers were separated and the aqueous layer was extracted with chloroform (2×100 ml). The organic solutions were combined and the solvent was evaporated. The resulting black solid was purified by chromatography on a silica gel column using methylene chloride as eluent. There was thus obtained 3-bromo-4-chloro-2,6-dimethylquinoline (5.9 g), m.p. 122°–125° C.

e: 3,4-Dichloro-2,6-dimethylquinoline, m.p. 80°–82° C., used as a starting material for the preparation of 6-bromomethyl-3,4-dichloro-2-methylquinoline was obtained from 2,6-dimethyl-4-quinolone using the two processes described in note d above except that N-chlorosuccinimide was used in place of N-bromosuccinimide in the first of those two processes.

f: 4-Chloro-2,3,6-trimethylquinoline used as a starting material for the preparation of 6-bromomethyl-4-chloro-2,3-dimethylquinoline was obtained from 2,3,6-trimethyl-4-quinolone (*Can. J. Chem.*, 1966, 44, 1863) using the second of the two processes described in note d above.

g: 4-Chloro-2,6,7-trimethylquinoline, m.p. 120°–122° C., used as a starting material for the preparation of 6-bromomethyl-4-chloro-2,7-dimethylquinoline was obtained from 2,6,7-trimethyl-4-quinolone (itself prepared by the reaction of 3,4-dimethylaniline and ethyl acetoacetate using the conditions described for the preparation of 2,6-dimethyl-4-quinolone in *J. Org. Chem.*, 1946, 11, 741) using the second of the two processes described in note d above.

The 6-bromomethylquinoline was obtained in admixture with the corresponding 7-bromomethylquinoline (7:3 6-bromomethyl: 7-bromomethyl) when the bromination process described in the portion of Example 1 concerned with the preparation of starting materials was carried out. The mixture of bromomethylquinolines was reacted with the appropriate diethyl N-[4-aminobenzoyl]-L-glutamate using the process described in Example 1 and the required diethyl N-[4-(N-quinolin-6-ylmethylamino)benzoyl]-L-glutamate was isolated by chromatography on a silica gel column using a 1:10 v/v mixture of ether and methylene chloride as eluent.

h: 4-Chloro-2-ethyl-6-methylquinoline used as a starting material for the preparation of 6-bromomethyl-4-chloro-2-ethylquinoline was obtained from 2-ethyl-6-methylquinolone (itself prepared by the reaction of p-toluidine and ethyl propionylacetate using the conditions described for the preparation of 2,6-dimethyl-4-quinolone in *J. Org. Chem.*, 1946, 11, 741) using the second of the two processes described in note d above.

i: 4-Bromo-2,6-dimethylquinoline, m.p. 55°–57° C., used as a starting material for the preparation of 4-bromo-6-bromomethyl-2-methylquinoline was obtained from 2,6-dimethylquinolone using the second of the two processes described in note d above except that phosphorus oxybromide was used in place of phosphorus oxychloride.

j: 4-Cyano-2,6-dimethylquinoline used as a starting material for the preparation of 6-bromomethyl-4-cyano-2-methylquinoline was obtained as follows:

A mixture of 4-bromo-2,6-dimethylquinoline (1.7 g, prepared as described in note i above), anhydrous cuprous cyanide (1.64 g) and dried DMF (25 ml) was heated at 140° C. for 6 hours. The resulting mixture was poured into a mixture of ice, water (40 ml) and ethylene diamine (1 ml) and extracted with ethyl acetate (4×100 ml). The combined extracts were evaporated and the residue was purified by chromatography on a silica gel column using a 1:4 v/v mixture of ethyl acetate and petroleum ether (b.p. 60°–80° C.) as eluent. There was thus obtained 4-cyano-2,6-dimethylquinoline (0.6 g), m.p. 113°–115° C.

k: 6-Bromomethyl-4-hydroxy-2-methylquinoline used as a starting material was obtained as follows:

A mixture of 6-cyano-2methyl-4-quinolone (9.2 g, *Chem. Abs.*, 51, 11347h; known therein as 6-cyano-4-hydroxyquinaldine), Raney nickel (10 g) and 75% formic acid (150 ml) was heated at reflux for 3 hours. The mixture was cooled, neutralised with a saturated aqueous solution of sodium bicarbonate and filtered. The solid residue was washed with warm methanol (3×50 ml). The combined filtrates were extracted with ethyl acetate (3×50 ml). The combined extracts were washed with water (100 ml), dried over sodium sulphate and evaporated to give 6-formyl-2-methyl-4-quinolone as a fawn coloured solid (9.3 g).

A mixture of this product (9.3 g), sodium borohydride (3.8 g) and ethanol (100 ml) was stirred at laboratory temperature for 18 hours. Water (50 ml) was added and the solution adjusted to pH 6 with aqueous N hydrochloric acid solution. The solution was evaporated to dryness. Methanol was added to the residue and the mixture was filtered. The filtrate was evaporated to give 6-hydroxymethyl-2-methyl-4-quinolone as an off-white solid (8.1 g), m.p. 249°–252° C.

A mixture of this product (8.1 g), phosphorus tribromide (11.8 g) and diethyl ether (150 ml) was heated at reflux for 2 hours. The mixture was cooled and poured into water (100 ml).

The product was filtered off and washed with diethyl ether. There was thus obtained 6-bromomethyl-4-hydroxy-2-methylquinoline (10.6 g), m.p. 190°–200° C.

l: 4-chloro-6-methyl-2-trifluoromethylquinoline used as a starting material for the preparation of 6-bromomethyl-4-chloro-2-trifluoromethylquinoline was obtained from 6-methyl-2-trifluoromethyl-4-quinolone (*J. Het. Chem.*, 1965, 2, 113) using the second of the two processes described in note d above.

m: Di-tert-butyl N-[4-(prop-2-ynyl)aminobenzoyl]-L-glutamate (UK Patent Specification No. 2188139A) was used. 2,4-Dichloro-6-methylquinoline, m.p. 90°–91° C., used as a starting material for the preparation of 6-bromomethyl-2,4-dichloroquinoline was obtaned from 4-hydroxy-6-methylcarbostyril using the second of the two processes described in note d above. The 4-hydroxy-6-methylcarbostyril was obtained by the reaction of p-toluidine and malonic acid using the method described (*Monat. Fur. Chemie*, 1967, 98. 324) for the preparation of 4-hydroxy-6-phenylcarbostyril.

n: 4-Chloro-2-methoxy-6-methylquinoline and 2-chloro-4-methoxy-6-methylquinoline used as starting materials for the preparation of 6-bromomethyl-4-chloro-2-methoxyquinoline and 6-bromomethyl-2-chloro-4-methoxyquinoline respectively were obtained as follows:

A mixture of 2,4-dichloro-6-methylquinoline (0.82 g, obtained as described in note m above), sodium methoxide (0.59 g) and methanol (15 ml) was stirred at 70° C. under an atmosphere of argon for 6 hours and then for a further 18 hours at laboratory temperature. The solvent was evaporated to give a white solid which was separated into the 4-chloro- and 2-chloro-quinolines by chromatography on a silica gel column using methylene chloride as eluent.

o: 2-Acetoxymethyl-4-chloro-6-methylquinoline used as a starting material for the preparation of 2-acetoxymethyl-6-bromomethyl-4-chloroquinoline was obtained as follows:

To a solution of 4-chloro-2,6-dimethylquinoline (4 g, described in the portion of Example 1 concerned with the preparation of starting materials) in chloroform (50 ml) was added dropwise a solution of m-chloroperbenzoic acid (6.75 g) in chloroform (50 ml). The resulting solution was stirred at laboratory temperature for 18 hours, washed with 10% aqueous sodium carbonate solution (2×50 ml) and with water (50 ml), and evaporated to dryness. The residue was purified by chromatography on a silica gel column using ethyl acetate as eluent. A mixture of the product so obtained (3 g) and acetic anhydride (30 ml) was stirred at 80° C. for 2 hours, the solvent was evaporated and a mixture of the residue and 10% aqueous hydrochloric acid (25 ml) was stirred at reflux for 30 minutes. The resulting mixture was cooled, basified to pH 14 with aqueous 2N sodium hydroxide solution, and extracted with ethyl acetate (3×50 ml). The organic extracts were combined and evaporated to drynes. The resulting brown solid was purified by chromatography on a silica gel column using a 3:2 v/v mixture of ethyl acetate and petroleum ether (b.p. 60°-80° C.) as eluent. There was thus obtained 4-chloro-2-hydroxymethyl-6-methylquinoline (2 g), m.p. 147°-148° C.

A mixture of this product (1 g), acetic anhydride (0.91 ml), pyridine (0.78 ml) and ethyl acetate (20 ml) was stirred at 60° C. for 18 hours. The resulting mixture was cooled, poured into water (50 ml) and extracted with ethyl acetate (3×20 ml). The organic extracts were combined and evaporated to dryness. The residue was purified by chromotagraphy on a silica gel column using a 7:20 v/v mixture of ethyl acetate and petroleum ether (b.p. 60°-80° C.) as eluent. There was thus obtained 2-acetoxymethyl-4-chloro-6-methylquinoline (0.58 g).

2,6-Dimethyl-4-methoxyquinoline used as a starting material for the preparation of 6-bromomethyl-4-methoxy-2-methylquinoline was obtained as follows:

A mixture of 4-chloro-2,6-dimethylquinoline (0.5 g, prepared as described in Example 1), sodium methoxide (0.42 g) and dry methanol (10 ml) were heated at reflux for 1 hour. After cooling to laboratory temperature a second portion of sodium methoxide (0.5 g) was added and the mixture was heated to reflux for a further 16 hours. The mixture was cooled to laboratory temperature, evaporated to dryness and the residue purified by chromatography on a silica gel column using a 19:1 v/v mixture of methylene chloride and methanol as eluent. There was thus obtained 2,6-dimethyl-4-methoxyquinoline (0.29 g).

q: 2-Chloro-4,6-dimethylquinoline, m.p. 97°-98° C., used as starting material for the preparation of 6-bromomethyl-2-chloro-4-methylquinoline was prepared by chlorination of 4,6-dimethyl-2-quinolone using the second of the two processes described in note d above.

r: 2,6-Dimethyl-4-methylthioquinoline used as a starting material for the preparation of 6-bromomethyl-2-methyl-4-methylthioquinoline was obtained as follows:

A mixture of 4-chloro-2,6-dimethylquinoline (0.5 g, prepared as described in Example 1), sodium thiomethoxide (0.55 g) and dry acetonitrile (20 ml) was heated to reflux under an atmosphere of argon for 15 hours. After cooling to laboratory temperature the mixture was poured into water (50 ml) and extracted with ethyl acetate (2×50 ml). The combined organic layers were dried over magnesium sulphate and evaporated to leave 2,6-dimethyl-4methylthioquinoline as a white solid (0.52 g) which was used without further purification.

s: 4-Chloro-6-methylquinoline-2-carboxamide used as a starting material for the preparation of 6-bromomethyl-4-chloroquinoline-2-carboxamide was obtained as follows:

Ethyl 6-methyl-4-quinolone-2-carboxylate (6.8 g, itself prepared from p-toluidine and diethyl acetylenedicarboxylate according to the general procedure outlined in *J. Med. Chem.*, 1968, 11. 1218), phosphorus oxychloride (2.2 ml), N,N-dimethylaniline (7.46 ml) and toluene (80 ml) were heated together for 3 hours at 90° C. and cooled to laboratory temperature. The mixture was poured into a mixture of ice and water (100 ml) and extracted with chloroform (4×100 ml). The combined extracts were evaporated and the resulting oil was purified by chromatography on a silica gel column using a 1:4 v/v mixture of ethyl acetate and petroleum ether (b.p. 60°-80° C.) as eluent. There was thus obtained as an oil ethyl 4-chloro-6-methylquinoline-2-carboxylate (4.2 g). A mixture of a portion (3.5 g) of this product and ethanol (80 ml) was stirred at laboratory temperature and an aqueous N sodium hydroxide solution was added. After stirring for 2 hours the mixture was carefully acidified to pH 2 by adding aqueous 2N hydrochloric acid solution. The precipitated solid was filtered off, washed with water and with ether and dried to leave 4-chloro-6-methylquinoline-2-carboxylic acid as an off-white solid (2.65 g). A mixture of a portion (1 g) of this product and thionyl chloride (10 ml) was gently heated at 80° C. for 1.5 hours and the excess of thionyl chloride was evaporated. The residue was dissolved in dry acetonitrile (25 ml) and added dropwise to an aqueous solution of ammonia (specific gravity 0.880, 25 ml). After stirring at room temperature for 1 hour the white precipitate was filtered off, washed with water and dried in air to leave 4-chloro-6-methylquinoline-2-carboxamide as an off-white powder (0.8 g) which was used without further purification.

t: 4-Chloro-2,6-dimethyl-8-fluoroquinoline, used as a starting material for the preparation of 6-bromoethyl-4-chloro-8-fluoro-2-methylquinoline, was obtained from 2,6-dimethyl-8-fluoro-4-quinolone (itself prepared from 2-fluoro-4-methylaniline and ethyl acetoacetate according to the general method described in *J. Org. Chem.*, 1946, 11, 741) using the procedure described in the first paragraph of the portion of Example 1 which relates to the preparation of starting materials.

u: 4-Chloro-2-fluoromethyl-6-methylquinoline, used as starting material for the preparation of 6-bromomethyl-4-chloro-2-fluoromethylquinoline, was obtained as follows: 4-Chloro-2-hydroxymethyl-6-methylquinoline (1 g), m.p. 147°-148° C. (obtained as described in note o above) was dissolved in dry methylene chloride (30 ml) and added dropwise to a mixture of diethylaminosulphur trifluoride (0.96 ml) in methylene chloride (10 ml) which was maintained at −70° C. by immersion in an acetone/dry-ice bath. After the addition was complete the mixture was allowed to warm to laboratory temperature, washed with water and evaporated. The residue was purified by chromatography on a silica gel column using methylene chloride as eluent. There was thus obtained 4-chloro-2-fluoromethyl-6-methylquinoline (0.28 g) which was used without further purification.

v: 2-Acetamido-4,6-dimethylquinoline, used as a starting material for the preparation of 2-acetamido-6-bromomethyl-4-methylquinoline was obtained as follows:

A mixture of 2-chloro-4,6-dimethylquinoline (3.8 g, prepared as described in note q above) and phenol (14 g)

was heated to 140° C. and dry ammonia gas was passed into the stirred mixture for 3 hours. After cooling the mixture was dissolved in an aqueous potassium hydroxide solution (10% w/v) and extracted with ethyl acetate (3×50 ml). The combined organic extracts were washed with aqueous N sodium hydroxide solution, dried (magnesium sulphate) and evaporated. The residue was purified by chromatography on a silica gel column using a 1:7 v/v mixture of methanol and ethyl acetate as eluent. There was thus obtained 2-amino-4,6-dimethylquinoline (0.4 g). A mixture of this product (0.4 g) and acetic anhydride (10 ml) was stirred at 20° C. for 3 hours and then evaporated to dryness. The residue was washed with petroleum ether (b.p. 60°–80° C., 3×25 ml) to leave 2-acetamido-4,6-dimethylquinoline as a pink solid (0.37 g).

w: After the coupling of 2-acetamido-6-bromomethyl-4-methylquinoline and diethyl N-[4-(prop-2-ynyl)aminobenzoyl]-L-glutamate using the process described in the first paragraph of Example 1 the resultant glutamate diester (0.33 g) was dissolved in ethanol (15 ml) and aqueous N sodium hydroxide solution (3.5 ml) was added. The mixture was stirred at 20° C. for 19 hours, the ethanol was evaporated and the solution was filtered and brought to pH 3 by adding aqueous 2N hydrochloric acid solution. The solid which was precipitated was separated, washed with water and dried. There was thus obtained N-[4-[N-(2-amino-4-methylquinolin-6-ylmethyl)-N-(prop-2-ynyl)]aminobenzoyl]-L-glutamic acid (0.17 g, containing 1.25 equivalents of water), m.p 205°–210° C.

x: 2-Bromo-4,6-dimethylquinoline used as a starting material for the preparation of 2-bromo-6-bromomethyl-4-methylquinoline was prepared as follows:

4,6-Dimethyl-2-quinolone (5.0 g) was suspended in toluene (50 ml) and phosphorus oxybromide (7.04 g) and N,N-dimethylaniline (7.3 ml) were added in succession. The mixture was heated to 90° C. for 3 hours, cooled, poured into a mixture of ice and water (100 ml) and extracted with chloroform (3×50 ml). The combined extracts were dried (over magnesium sulphate) and evaporated and the residue was chromatographed on a silica gel column using increasingly polar mixtures of petroleum ether (b.p. 60°–80° C.) and methylene chloride as eluent. There was thus obtained 2-bromo-4,6-dimethylquinoline as a white solid (1 g).

y: The 2-chloro-6-methylquinoline required as a starting material for the preparation of 6-bromomethyl-2-chloroquinoline was prepared as follows:

Cinnamoyl chloride (18.88 g) in methylene chloride (100 ml) was added dropwise to a cold (ice-bath), stirred solution of p-toluidine (12.14 g) and pyridine (9.14 ml) in methylene chloride (400 ml). The mixture was stirred for 3 hours and allowed to warm to room temperature. The mixture was washed in succession with water (2×100 ml), 2N hydrochloric acid solution (2×100 ml) and water (2×100 ml). The organic layer was evaporated and there was thus obtained N-p-tolylcinnanamide (28.65 g).

An intimate mixture of a portion (5.4 g) of the product so obtained and freshly ground aluminum trichloride (16.2 g) was carefully heated until a vigorous reaction began. After the reaction has subsided the mixture was heated on a steam bath for 1 hour and then carefully poured into a mixture of ice and water. The resultant precipitate was filtered off, washed with 2N hydrochloric acid solution and with water and dried. There was thus obtained 6-methyl-2-quinolone (4.35 g). A mixture of a portion (3.11 g) of the product so obtained, phosphorus oxychloride (6.0 g) and toluene (20 ml) was heated at 85° C. for 2.5 hours, cooled and poured onto crushed ice (50 g). The mixture was basified by adding aqueous potassium hydroxide solution (15% w/v) and extracted with methylene chloride (3×25 ml). The combined organic extracts were washed with water (2×25 ml) and evaporated. The crude product was purified by column chromatography on a silica gel column using increasingly polar mixtures of hexane and methylene chloride as eluent to give 2-chloro-6-methylquinoline as a white solid (2.22 g).

z: 2,3-Dichloro-6-methylquinoline used as a starting material for the preparation of 6-bromomethyl-2,3-dichloroquinoline was prepared by reacting N-p-tolyl-2-chloroacetamide, phosphorus oxychloride and dimethylformamide according to the general procedure described in Tet. Let., 1979, 4885.

EXAMPLE 3

The process described in Example 1 was repeated using the appropriate 6-bromomethylquinoline and, unless otherwise stated in a footnote, the appropriate diethyl N-[4-aminobenzoyl]-L-glutamate as starting materials. All of the 6-bromomethylquinolines were prepared from the corresponding 6-methylquinolines (prepared as described in Examples 1 and 2) using the bromination process described in the portion of Example 1 concerned with the preparation of starting materials. All the diethyl N-[4-aminobenzoyl]-L-glutamates were obtained as described in UK Patent Specification No. 2188319A. There were thus obtained the compounds described in the following table, the structures of which were confirmed by proton magnetic resonance and mass spectroscopy and by elemental analysis.

TABLE II

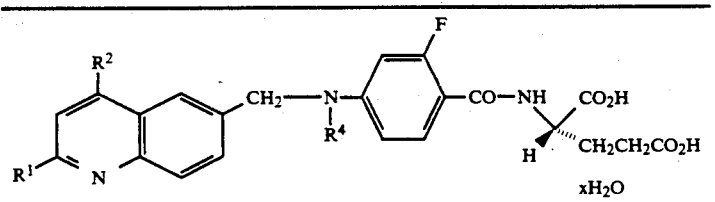

| Ex. 3 Compound No. | $R^1$ | $R^2$ | $R^4$ | x | m.p. (°C.) |
|---|---|---|---|---|---|
| 1 | Me | Cl | Et | 1 | 135 |
| 2 | Me | Cl | Me | 1.5 | 132–137 |
| 3 | Me | Cl | H | 1.5 | 129 |
| 4 | Me | Br | CH$_2$C≡CH | 1.5 | 121–124 |
| 5 | Cl | Cl | CH$_2$C≡CH | 1 | 88–94 |
| 6$^a$ | Cl | Me | CH$_2$C≡CH | 1.3 | 110–120 |

TABLE II-continued

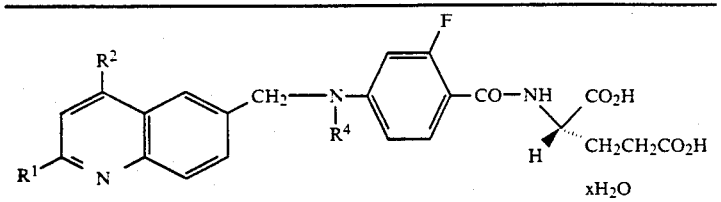

| Ex. 3 Compound No. | R¹ | R² | R⁴ | x | m.p. (°C.) |
|---|---|---|---|---|---|
| 7[b] | | NH₂ | Cl | CH₂C≡CH | 2.2 | 165-170 | a: Di-tert-butyl N-[2-fluoro-4-(prop-2-ynyl)aminobenzoyl]-L-glutamate was used in place of the corresponding diethyl ester. The di-tert-butyl ester was obtained by alkylation of di-tert-butyl N-[4-aminobenzoyl]-L-glutamate (Journal of Medicinal Chemistry, 1983, 26, 1193) with propargyl bromide using the procedures described in UK Patent Specification No. 2188319A for the alkylation of diethyl N-[4-aminobenzoyl]-L-glutamate. After the coupling of the di-tert-butyl ester and 6-bromomethyl-2-chloro-4-methylquinoline using the process described in the first paragraph of Example 1 the purified product was hydrolysed with base using the process described in the second paragraph of Example 1 except that the reaction mixture was stirred as laboratory temperature for 4 hours and was then stored at a temperature of 5° C. for 60 hours.

b: The process described in the first paragraph of Example 1 was used to couple 2-acetamide-6-bromomethyl-4-chloroquinoline and di-tert-butyl N-[2-fluoro-4-(prop-2-ynyl)aminobenzoyl]-L-glutamate.

The purified product (0.33 g) was dissolved in ethanol (10 ml), aqueous N sodium hydroxide solution (3 ml) was added and the mixture was heated to 40° C. for 2.5 hours. The ethanol was evaporated and the solid residue was filtered off, dried and dissolved in trifluoroacetic acid (10 ml). The mixture was stirred at laboratory temperature for 30 minutes and then evaporated. The residue was dissolved in aqueous N sodium hydroxide solution, filtered and adjusted to pH 3 by the addition of 2N hydrochloric acid solution. The solid which was precipitated was filtered off, washed with water and dried.

2-Acetamido-4-chloro-6-methylquinoline, used as a starting material for the preparation of 2-acetamido-6-bromomethyl-4-chloroquinoline was obtained as follows:

A mixture of 4-chloro-6-methylquinoline-2-carboxylic acid (1.3 g, prepared as described in Example 2, note s), tert-butanol (30 ml), dimethylformamide (40 ml), diphenylphosphoryl azide (1.3 ml) and triethylamine (1.6 ml) was heated to 100° C. for 7 hours. The mixture was allowed to cool to laboratory temperature. Evaporation gave a black oil which was purified by chromatography on a silica gel column using methylene chloride as eluent. There was thus obtained 2-(tert-butoxycarbonylamino)-4-chloro-6-methylquinoline (1.12 g) which was used without further purification.

A portion (1.04 g) of this material was dissolved in trifluoroacetic acid (15 ml) and the mixture was stirred at 20° C. for 30 minutes. The trifluoroacetic acid was evaporated, the residue was dissolved in acetic anhydride (10 ml) and the mixture was stirred at 20° C. for 3 hours. The mixture was evaporated and the residue was chromatographed on a silica gel column using increasingly polar mixtures of methylene chloride and ethyl acetate as eluent to give 2-acetamido-4-chloro-6-methylquinoline (0.78 g).

EXAMPLE 4

The process described in Example 1 was repeated except that diethyl N-(5-ethylamino-2-thenoyl)-L-glutamate (prepared as described in UK Patent Specification No. 2188319A) was used in place of diethyl N-[2-fluoro-4-(prop-2-ynyl)aminobenzoyl]-L-glutamate. There was thus obtained N-[5-[N-(4-chloro-2-methylquinolin-6-ylmethyl)-N-ethylamino]-2-thenoyl]-L-glutamic acid (containing 1.5 equivalents of water), m.p. 98°-105° C.

NMR Spectrum: (CD₃SOCD₃) 1.19 (t, J=7 Hz, 3H, CH₂C$\underline{H}_3$), 1.89 (m, 2H, CH₂), 2.28 (m, 2H, C$\underline{H}_2$CO₂H), 2.64 (s, 3H, CH₃), 3.49 (quarter, J=6.5 Hz, 2H, C$\underline{H}_2$CH₃), 4.74 (m, 1H, NHC$\underline{H}$), 4.76 (s, 2H, CH₂N), 5.94 (d, J=4 Hz, 1H, aromatic), 7.47 (d, J=4 Hz, 1H, aromatic), 7.66 (s, 1H, aromatic), 7.71 (d of d's, J=2 and 8.5 Hz, 1H, aromatic), 7.83 (m, 1H, NH), 7.98 (d, J=8.5 Hz, 1H, aromatic), 8.02 (d, J=1.5 Hz, 1H, aromatic).

Mass Spectrum: (positive ion FAB) m/e 490 (P+1).

Elemental Analysis: Found C, 53.4; H, 5.0; N, 8.0; C₂₃H₂₄ClN₃O₅S. 1.5 H₂O requires C, 53.4; H, 5.2; N, 8.1%.

EXAMPLE 5

A mixture of 6-bromomethyl-4-methoxy-2-pivaloylamino quinoline (0.2 g), diethyl N-(4-ethylaminobenzoyl)-L-glutamate (0.2 g), 2,6-lutidine (0.4 ml) and dimethylacetamide (5 ml) was stirred at 60° C. for 18 hours under an atmosphere of argon. The mixture was cooled, poured into water (50 ml) and extracted with ethyl acetate (3×50 ml). The combined extracts were washed with water (2×50 ml), dried over magnesium sulphate and evaporated. The resulting gum was purified by chromatography on a silica gel column using a 1:1 v/v mixture of ethyl acetate and petroleum ether (b.p. 60°-80° C.) as eluent.

A mixture of the product so obtained (0.2 g), ethanol (5 ml) and aqueous N sodium hydroxide solution (1.6 ml) was stirred at 65° C. under argon for 18 hours. The solution was cooled and filtered and the filtrate was evaporated. The residue was dissolved in deionised water and the solution was acidified to pH 4 by adding 2N hydrochloric acid solution. The mixture was filtered and the solid residue was washed with de-ionised water and dried. There was thus obtained N-[4-[N-(2amino-4-methoxyquinolin-6-ylmethyl)-N-ethylamino]benzoyl]-L-glutamic acid (containing 2 equivalents of water; 0.14 g), m.p. 200°-206° C.

NMR Spectrum: (CD₃SOCD₃) 1.15 (t, J=6.5 Hz, 3H, CH₂C$\underline{H}_3$), 1.99 (m, 2H, CH₂), 2.30 (t, J=7.5 Hz, 2H, C$\underline{H}_2$CO₂$\underline{H}$), 3.53 (m, 2H, C$\underline{H}_2$CH₃), 3.9 (s, 3H, OCH₃), 4.35 (m, 1H, NHCH), 4.65 (s, 2H, CH₂N), 6.20 (s, 1 H, aromatic), 6.51 (m, 2H, NH₂), 6.70 (d, J=9 Hz, 2H, aromatic), 7.37 (broad s, 2H, aromatic), 7.68 (m, 3H, aromatic), 8.08 (d, J=7.5 Hz, 1H, NH).

Mass Spectrum: (positive ion FAB) m/e 481 (P+1).
Elemental Analysis: Found C, 57.8; H, 6.0; N, 10.4; $C_{25}H_{28}N_4O_6$. 2 $H_2O$ requires C, 58.1; H, 6.2; N, 10.8%.

The quinoline used as starting material was obtained as follows:

A mixture of 2-amino-6-methyl-4-quinolone (3.1 g, *Synthesis*, 1977, 500) and methyl p-toluenesulphonate (3.32 g) was stirred at 120° C. for 30 minutes and left to stand at laboratory temperature for 18 hours. The resulting solid was triturated with aqueous 2N sodium hydroxide solution (100 ml) to give a solid which was filtered off, washed with water (2×100 ml) and dried. There was thus obtained 2-amino-4-methoxy-6-methylquinoline (2.13 g). Pivaloyl chloride (0.64 g) was added dropwise to a stirred mixture of 2-amino-4-methoxy-6-methylquinoline 1 g), triethylamine (0.85 ml) and dimethylformamide (17 ml). The resulting solution was stirred at laboratory temperature for 18 hours, poured into water (100 ml) and extracted with ethyl acetate (3×50 ml). The combined extracts were washed with water (50 ml), dried over sodium sulphate and evaporated. The resulting solid was purified by chromatography on a silica gel column using a 3:10 v/v mixture of ethyl acetate and petroleum ether (b.p. 60°-80° C.) as eluent. There was thus obtained 4-methoxy-6-methyl-2-pivaloylaminoquinoline (0.535 g), m.p. 75°-76° C.

A mixture of this product (0.5 g), N-bromosuccinimide (0.35 g), benzoyl peroxide (9 mg) and carbon tetrachloride (50 ml) was heated at reflux for 24 hours during which time the mixture was illuminated by the light from a 250 Watt light bulb. The resulting mixture was filtered and the filtrate was evaporated to give a yellow foam which was purified by chromatography on a silica gel column using a 3:20 v/v mixture of ethyl acetate and petroleum ether (b.p. 60°-80° C.) as eluent. There was thus obtained 6-bromomethyl-4-methoxy-2-pivaloylaminoquinoline (0.21 g).

EXAMPLE 6

The process described in Example 1 was repeated except that ethyl N-[4-(prop-2-ynyl)aminobenzoyl]-L-valinate was used in place of diethyl N-[2-fluoro-4-(prop-2-ynyl)aminobenzoyl]-L-glutamate. There was thus obtained N-[4-[N-(4-chloro-2-methylquinolin-6-ylmethyl)-N-(prop-2-ynyl)amino]benzoyl]-L-valine containing 1.25 equivalents of water, m.p. 100°-105° C.

NMR Spectrum: (CD₃SOCD₃) 0.95 (d, J=6.5 Hz, 3H, CH₃), 0.96 (d, J=6.5 Hz; 3H, CH₃), 2.14 (octet, J=6.5 Hz, 1H, CH), 2.64 (s, 3H, CH₃), 3.23 (t, J=1 Hz, 1H, C≡CH), 4.25 (d of d's, J=6.5 and 7.5 Hz, 1H, CHCO₂H), 4.39 (broad s, 2H, CH₂C≡CH), 4.91 (broad s, 2H, CH₂N), 6.87 (d, J=10 Hz, 2H, aromatic), 7.66 (s, 1H, aromatic), 7.76 (m, 3H, aromatic and NH), 7.97 (d, J=10 Hz, 2H, aromatic), 8.08 (d, J=1.5 Hz, 1H, aromatic), 12.46 (broad s, 1H, CO₂H).

Mass Spectrum: (negative ion FAB) m/e 462 (P−1).
Elemental Analysis: Found C, 63.8; H, 5.5; N 8.3 ; $C_{26}H_{26}ClN_3O_3$. 1.25 $H_2O$ requires C, 64.2; H, 5.9; N, 8.6%.

The ethyl N-[4-(prop-2-ynyl)aminobenzoyl]-L-valinate used as a starting material was prepared from ethyl valinate hydrochloride in an analogous manner to the preparation of diethyl N-[4-(prop-2-ynyl)aminobenzoyl]-L-glutamate from diethyl glutamate hydrochloride as described in *J. Med. Chem.*, 1986, 29, 1114.

EXAMPLE 7

A mixture of 6-bromomethyl-4-chloro-2-methylquinoline (0.3 g), diethyl N-[5-methylaminothiazole-2-carbonyl]-L-glutamate (0.38 g, prepared as described in UK Patent Specification No. 2202847A, 2,6-lutidine 0.13 ml) and dimethylformamide (10 ml) was heated at 70° C. for 18 hours under an atmosphere of argon. The mixture was cooled to laboratory temperature, poured into water (50 ml) and extracted with ethyl acetate (3×30 ml). The combined organic extracts were washed with water and evaporated. The residue was purified by column chromatography on a silica gel column using ether as eluent.

A mixture of the product so obtained (0.21 g), ethanol (5 ml) and aqueous N sodium hydroxide solution (1.6 ml) was stirred at 20° C. for 3 hours. The ethanol was evaporated and the aqueous solution was filtered and acidified to pH 3 by adding 2N hydrochloric acid solution. The precipitate was filtered off, washed with water and dried. There was thus obtained N-[5-[N-(4-chloro-2-methylquinolin-6-ylmethyl)-N-methylamino]thiazole-2-carbonyl]-L-glutamic acid (0.15 g, containing 0.5 equivalents of water), m.p. 220°-225° C.

NMR Spectrum: (CD₃SOCD₃) 1.85-2.2 (m, 2H, CH₂), 2.28 (t, J=7 Hz, 2H, CH₂COOH), 2.66 (s, 3H, CH₃), 3.13 (s, 3H, NCH₃), 4.28-4.43 (m, 1H, NHCHCOOH), 4.82 (s, 2H, CH₂N), 7.09 (s, 1H, aromatic), 7.72 (s, 1H, aromatic), 7.74 (d of d's, J=7 and 1.5 Hz, 1H, aromatic), 8.01 (d, J=7 Hz, 1H, aromatic), 8.05 (d, J=1.5 Hz, aromatic), 8.35 (d, J=8 Hz, 1H, NH).

Mass spectrum: (negative ion FAB) m/e 475 (P−1).
Elemental Analysis: Found C, 51.8; H, 4.4; N, 10.6; $C_{21}H_{21}ClN_4O_5S$. 0.5 $H_2O$ rquires C, 51.9; H, 4.6; N, 11.5%.

EXAMPLE 8

The process described in Example 7 was repeated except that 6-bromomethyl-2,4-dichloroquinoline was used in place of 6-bromomethyl-4-chloro-2-methylquinoline. There was thus obtained N-[5-[N-(2,4-dichloroquinolin-6-ylmethyl)-N-methylamino]thiazole-2-carbonyl]-L-glutamic acid (containing 0.5 equivalents of water), m.p. 200°-205° C., the structure of which was confirmed by proton magnetic resonance and mass spectroscopy and by elemental analysis.

EXAMPLE 9

The process described in Example 4 was repeated using the appropriate 6-bromomethylquinoline and diethyl N-(5-methylamino-2-thenoyl)-L-gluatmate (prepared as described in UK Patent Specification No. 2188319 A). There were thus obtained the compounds described in the following table, the structures of which were confirmed by proton magnetic resonance and mass spectroscopy and by elemental analysis.

TABLE III

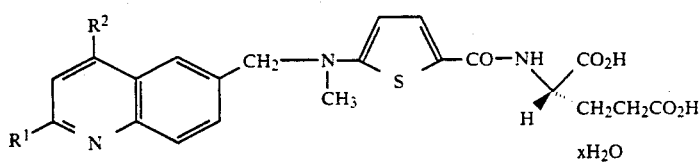

| Example 9 Compound No. | R¹ | R² | x | m.p. (°C.) |
| --- | --- | --- | --- | --- |
| 1 | Me | Cl | 1 | 160–165 |
| 2 | Cl | Cl | 0.5 | 125–130 |
| 3ᵃ | NH₂ | Cl | 1.3 | 210–215 | a: 2-(tert-Butoxycarbonylamino)-4-chloro-6-methylquinoline (prepared as described in note b in Example 3) was used as a starting material and reacted with the diethyl L-glutamate using the process described in the first paragraph of Example 1. The product (0.37 g) so obtained was dissolved in trifluoroacetic acid (10 ml) and stirred at 20° C. for 1 hour. The mixture was evaporated and the residue was purified by chromatography on a silica gel column using a 19:1 v/v mixture of diethyl ether and methanol as eluent. There was thus obtained diethyl N-[5-[N-(2-amino-4-chloroquinolin-6-ylmethyl)-N-methylamino]-2-thenoyl]-L-glutamate (0.33 g) which was treated with aqueous sodium hydroxide solution using the process described in the second paragraph of Example 1.

EXAMPLE 10

A mixture of 2-acetamido-6-bromomethyl-4-chloroquinoline (0.62 g, prepared as described in note b in Example 3), di-tert-butyl N-[4-(prop-2-ynyl)aminobenzoyl]-L-glutamate (0.82 g), 2,6-lutidine (0.23 g) and dimethylformamide (30 ml) was heated at 70° C. for 18 hours under an atmosphere of argon. The mixture was cooled to laboratory temperature, poured into water (100 ml) and extracted with ethyl acetate (3×40 ml). Evaporation of the combined organic extracts left a brown gum which was purified by column chromatography on a silica gel column using increasingly polar mixtures of petroleum ether (b.p. 60°–80° C.) and diethyl ether as eluent.

A mixture of the product so obtained (130 mg) and trifluoroacetic acid (2 ml) was stirred for 0.8 hours at 20° C. under an atmosphere of argon. The mixture was evaporated. The residue was dissolved in aqueous N sodium hydroxide solution, filtered and then acidified to pH 3 by the addition of 2N hydrochloric acid solution. The precipitate was isolated by filtration, washed with water and dried. There was thus obtained N-[4-[N-(2-acetamido-4-chloroquinolin-6-ylmethyl)-N-(prop-2-ynyl)amino]benzoyl]-L-glutamic acid (0.08 g, containing 0.8 equivalents of trifluoroacetic acid), m.p. 160°–165° C. NMR Spectrum: (CD₃SOCD₃) 1.82–2.2 (m, 2H, CH₂), 2.15 (s, 3H, CH₃CONH), 2.33 (t, J=7 Hz, 2H, CH₂COOH), 3.25 (broad s, 1H C≡CH), 4.28–4.43 (m, 3H, NHCHCOOH and NCH₂C≡C), 4.89 (s, 2H, CH₂N), 6.87 (d, J=8 Hz, 2H, aromatic), 7.7–7.88 (m, 4H, aromatic), 8.04 (d, J=1.5 Hz, 1H, aromatic), 8.22 (d, J=7 Hz, 1H, NH), 8.46 (s, 1H, aromatic).

Mass Spectrum: (negative ion FAB) m/e 535 (P-1).
Elemental analysis: Found C, 54.7; N, 4.4; N, 9.1; C₂₇H₂₅ClN₄O₆. 0.8 CF₃COOH requires C, 54.7; H, 4.2; N, 18.9%.

EXAMPLE 11

A mixture of 6-bromomethyl-2-(tert-butoxycarbonylamino)-4-chloroquinoline (0.40 g), diethyl N-[4-(prop-2-ynyl)aminobenzoyl]-L-glutamate (0.38 g), 2,6-lutidine (0.125 ml) and dry dimethylformamide (15 ml) was heated at 70° C. for 12 hours under an atmosphere of argon. The mixture was cooled, poured into water (60 ml) and extracted with ethyl acetate (4×40 ml). Evaporation of the combined organic extracts left a brown oil which was purified by chromatography on a silica gel column using ether as eluent.

A mixture of the material so obtained (0.22 g) and trifluoroacetic acid (3.5 ml) was stirred at 20° C. for 30 minutes under an atmosphere of argon. The mixture was evaporated and the residue was purified by chromatography on a silica gel column using initially ether and then a 19:1 v/v mixture of ether and methanol. The material (130 mg) so obtained was dissolved in ethanol (7 ml), aqueous N sodium hydroxide solution (1.4 ml) was added and the mixture was stirred at 20° C. for 2.5 hours. The mixture was evaporated, the aqueous solution was filtered and then acidified to pH 3 by adding 2N hydrochloric acid solution. The precipitate was filtered off, washed with water and dried. There was thus obtained N-[4-[N-(2-amino-4-chloroquinolin-6-ylmethyl)-N-(prop-2-ynyl)amino]benzoyl]-L-glutamic acid (60 mg; containing 1.5 equivalents of water), m.p. 177°–179° C. NMR spectrum: (CD₃SOCD₃) 1.85–2.2 (m, 2H, CH₂), 2.32 (t, J=6.5 Hz, 2H, CH₂COOH), 3.20 (s, 1H, C≡CH), 4.28–4.45 (m, 3H, NHCHCOOH and CH₂ C≡C), 4.79 (s, 2H, CH₂N), 6.86 (d, J=8 Hz, 2H, aromatic), 6.91 (broad s, 2H, NH₂), 6.99 (s, 1H, aromatic), 7.5–7.6 (m, 2H, aromatic), 7.75 (d, J=8 Hz, 2H, aromatic), 7.86 (s, 1H, aromatic), 8.21 (d, J=10 Hz, 1H, CONH).

Mass Spectrum (negative ion FAB) m/e=493 (P-1).
Elemental Analysis: Found C, 57.4; H, 4.7; N, 10.5; C₂₅H₂₃ClN₄O₅. 1.5 H₂O requires C, 57.5; H, 5.0; N, 10.7%.

EXAMPLE 12

A mixture of 6-bromomethyl-3-(tert-butoxycarbonylamino)-4-chloroquinoline (0.22 g), diethyl N-[4-(prop-2-ynyl)aminobenzoyl]-L-glutamate (0.15 g), 2,6-lutidine (0.072 ml) and dry dimethylformamide (2 ml) was stirred and heated to 70° C. under an atmosphere of argon for 18 hours. The mixture was cooled, poured into water (10 ml) and extracted with ethyl acetate (3×10 ml). The combined extracts were dried over magnesium sulphate and evaporated to leave a gum which was purified by chromatography on a silica gel column using increasingly polar mixtures of methylene chloride and ethyl acetate as eluent.

A mixture of the product so obtained (0.15 g) and trifluoroacetic acid (2 ml) was stirred at 20° C. for 30 minutes. The mixture was evaporated and the residue was purified by chromatography on a silica gel column using increasingly polar mixtures of methylene chloride and ethyl acetate as eluent.

A mixture of the product so obtained (0.11 g), ethanol (2 ml) and aqueous N sodium hydroxide solution (1 ml) was stirred at 20° C. under an atmosphere of argon for 2 hours. The ethanol was evaporated and the resulting aqueous solution was filtered and acidified to pH 3 by adding 2N hydrochloric acid solution. The precipitated solid was filtered off, washed with water and dried. There was thus obtained N-[4-[N-(3-amino-4-chloroquinolin-6-ylmethyl)-N-(prop-2-ynyl)amino]benzoyl]L-glutamic acid (containing 1.5 equivalents of water, 0.066 g), m.p. 140°-150° C.

NMR spectrum: ($CD_3SOCD_3$) 1.84-2.19 (m, 2H, $CH_2$), 2.34 (t, J=7 Hz, 2H, $CH_2COOH$), 3.22 (t, J=1 Hz, 1H, C≡CH), 3.4 (broad s, 2H, $NH_2$), 4.28-4.43 (m, 3H, NHCH and $CH_2C$≡CH), 4.86 (broad s, 2H, $CH_2N$), 6.86 (d, J=9 Hz, 2H, aromatic), 7.38 (d of d's, J=1.7 and 8.5 Hz, 1H, aromatic), 7.74 (d, J=9 Hz, 2H, aromatic), 7.82 (d, J=1.7 Hz, 1H, aromatic), 7.84 (d, J=8.5 Hz, 1H, aromatic), 8.19 (broad d, J=13 Hz, 1H, NH), 8.53 (s, 1H, aromatic).

Mass Spectrum: (negative ion FAB) m/e 493 (P-1).

Elemental Analysis: Found C, 59.4; H, 4.7; N, 10.8; $C_{25}H_{23}N_4O_5Cl$. 1.5 $H_2O$ requires C, 59.1; H, 5.2; N, 8.3%.

The quinoline used as starting material was obtained as follows:

A mixture of ethyl 6-methyl-4-quinolone-3-carboxylate (1.8 g, *J. Chem. Soc.* 1948, 893), N,N-dimethylaniline (1.9 ml), phosphorus oxychloride (0.6 ml) and toluene (25 ml) was heated to 90° C. for 3 hours. The solution was cooled to laboratory temperature and poured into ice-water (20 ml) and extracted with chloroform (4×25 ml). The combined extracts were evaporated to leave a purple solid which was purified by chromatography on a silica gel column using chloroform as eluent. There was thus obtained ethyl 4-chloro-6-methylquinoline-3-carboxylate (1.46 g).

A mixture of this product (4.6 g), ethanol (100 ml) and aqueous N sodium hydroxide solution (50 ml) was stirred at 20° C. under an atmosphere of argon for 3 hours. Ethanol was evaporated and the solution acidified with 2N aqueous hydrochloric acid solution to pH 2. The precipitated solid was filtered off, washed with water and dried. There was thus obtained 4-chloro-6-methylquinoline-3-carboxylic acid (3.4 g).

A mixture of this acid (3.46 g), diphenylphosphoryl azide (3.4 ml), tert-butanol (78 ml), dimethylformamide (104 ml) and triethylamine (4.4 ml) was heated to 100° C. for 7 hours, cooled and evaporated. The residue was purified by chromatography on a silica gel column using methylene chloride as eluent. There was thus obtained 3-(tert-butoxycarbonylamino)-4-chloro-6-methylquinoline (2.44 g).

A mixture of a portion (0.5 g) of the product so obtained, N-bromosuccinimide (0.36 g), benzoyl peroxide (0.02 g) and carbon tetrachloride (30 ml) was heated to reflux for 3 hours during which time the mixture was illuminated by the light from a 250 Watt light bulb. The mixture was cooled, filtered and evaporated. The yellow residue was purified by chromatography on a silica gel column using a 1:12 v/v mixture of ethyl acetate and methylene chloride as eluent. There was thus obtained 6-(bromomethyl)-3-(tert-butoxycarbonylamino)-4-chloroquinoline (0.22 g).

EXAMPLE 13

A mixture of 6-(1-bromoethyl)-4-chloro-2-methylquinoline (0.65 g), diethyl N-[4-(prop-2-ynyl)aminobenzoyl]-L-glutamate (0.86 g), 2,6-lutidine (0.6 ml) and dry dimethylformamide (10 ml) was stirred and heated to 70° C. under an atmosphere of argon for 30 hours. The mixture was cooled to laboratory temperature, poured into water (20 ml) and extracted with ethyl acetate (3×20 ml). The combined organic extracts were evaporated and the residue was purified by chromatography on a silica gel column using diethyl ether as eluent.

A mixture of the product so obtained (0.22 g), ethanol (5 ml) and aqueous N sodium hydroxide solution (2.2 ml) was stirred at laboratory temperature under argon for 2.5 hours. The mixture was evaporated, the residue was diluted with water (2 ml) and then acidified to pH 3 by adding 2N hydrochloric acid solution. The precipitated solid was filtered off, washed with water and dried. There was thus obtained N-[4-[N-(1-(4-chloro-2-methylquinolin-6-yl)ethyl)-N-(prop-2-ynyl)amino]benzoyl]-L-glutamic acid (0.15 g, containing 1 equivalent of water), m.p. 160°-165° C.

NMR spectrum: ($CD_3SOCD_3$) 1.74 (d, 3H, $CHCH_3$, J=6.5 Hz), 1.85-2.17 (m, 2H, $CH_2$), 2.33 (t, 2H, $CH_2COOH$, J=7.5 Hz), 2.64 (s, 3H, $CH_3$), 3.13 (broad s, 1H, C≡CH), 4.00-4.25 (m, 2H, $CH_2C$≡CH), 4.27-4.45 (m, 1H, NHCH), 5.51 (q, 1H, $CHCH_3$, J=6.5 Hz), 6.95 (d, 2H, aromatic, J=8.5 Hz), 7.68 (s, 1H, aromatic), 7.75-7.80 (m, 3H, aromatic), 7.96 (d, 1H, aromatic, J=9 Hz), 8.08 (d, 1H, aromatic, J=1 Hz), 8.21 (d, 1H, NH, J=7 Hz).

Mass Spectrum: (negative ion FAB) m/e 506 (P-1).

Elemental analysis: Found C, 61.6; H, 5.1; N, 7.7; $C_{27}H_{26}N_3O_5Cl$. 1 $H_2O$ requires C, 61.6; H, 5.4; N, 8.0%.

The 6-(1-bromoethyl)-4-chloro-2-methylquinoline, used as a starting material, was obtained as follows:

A mixture of 6-ethyl-2-methyl-4-quinolone (4.61 g, itself obtained from 4-ethylaniline and ethyl acetoacetate according to the general procedure described in *J. Org. Chem.* 1946, 11, 741), phosphorus oxychloride (1.54 ml), N,N-dimethylaniline (6.15 ml) and dry toluene (30 ml) was heated at 90° C. for 3 hours. The resulting solution was poured onto ice (30 g) and the mixture was extracted with chloroform (3×100 ml). The combined extracts were evaporated and the residue was chromatographed on a silica gel column using increasingly polar mixtures of petroleum ether (b.p. 60°-80° C.) and ethyl acetate as eluent. There was thus obtained 4-chloro-6-ethyl-2-methylquinoline (3.2 g).

This material was converted to 6-(1-bromoethyl)-4-chloro-2-methylquinoline using N-bromosuccinimide by a process analogous to that described in the second paragraph of Example 1.

EXAMPLE 14

A mixture of 6-bromomethyl-2,3-dichloroquinoline (0.35 g), di-tert-butyl N-[2-fluoro-4-(prop-2-ynyl)aminobenzoyl]-L-glutamate (0.53 g), 2,6-lutidine (0.29 ml) and N,N-dimethylacetamide (10 ml) was heated to 75° C. for 12 hours under an atmosphere of argon. After cooling to laboratory temperature the mixture was poured into water (25 ml) and extracted with ethyl acetate (4×10 ml). The combined extracts were dried over magnesium sulphate and evaporated. The residue was purified by column chromatography on a silica gel column using increasingly polar mixtures of methylene chloride and ethyl acetate as eluent to give a pale foam (0.32 g).

A mixture of the product so obtained (0.311 g) and trifluoroacetic acid (2 ml) was stirred at 20° C. for 2 hours. The mixture was evaporated, the residue was dissolved in saturated aqueous sodium bicarbonate solution and the solution was filtered and acidified to pH 3 by adding 2N hydrochloric acid solution. The precipitated solid was filtered off, washed with water and dried. There was thus obtained N-[4-[N-(2,3-dichloroquinolin-6-ylmethyl)-N-(prop-2-ynyl)amino]-2-fluorobenzoyl]-L-glutamic acid, (containing 1.08 equivalents of trifluoroacetic acid, 0.19 g), m.p. 98°-102° C.

NMR Spectrum: (CD$_3$SOCD$_3$) 1.84-2.15 (m, 2H, CH$_2$), 2.29 (t, J=6.5 Hz, 2H, CH$_2$COOH), 3.28 (broad s, 1H, C≡CH), 4.3-4.5 (m, 3H, NCH$_2$C≡C and NHCHCO), 4.89 (s, 2H, CH$_2$N), 6.6-6.75 (m, 2H, aromatic), 7.56 (t, J=7 Hz, 1H, aromatic), 7.75-8.0 (m, 4H, aromatic and NH), 8.73 (s, 1H, aromatic).

Mass Spectrum: (negative ion FAB) m/e 530 (P-1).

Elemental Analysis: Found; C, 49.8; H, 3.4; N, 6.8; C$_{25}$H$_{20}$N$_3$O$_5$Cl$_2$F. 1.08 CF$_3$COOH requires C, 49.9; H, 3.1; N, 6.4%.

EXAMPLE 15

The process described in Example 11 was repeated except that diethyl N-[5-methylaminothiazole-2-carbonyl]-L-glutamate was used in place of diethyl N-[4-(prop-2-ynyl)aminobenzoyl]-L-glutamate. There was thus obtained N-[5-[N-(2-amino-4-chloroquinolin-6-ylmethyl)-N-methylamino]thiazole-2-carbonyl]-L-glutamic acid (containing 1.5 equivalents of water).

NMR Spectrum: 1.9-2.22 (m, 2H, CH$_2$), 2.29 (t, J=7 Hz, 2H, CH$_2$COOH), 3.1 (s, 3H, CH$_3$), 4.29-4.44 (m, 1H, NHCHCO), 4.7 (s, 2H, CH$_2$N), 7.04 (s, 1H, aromatic), 7.09 (s, 1H, aromatic), 7.59 (broad s, 2H, aromatic), 7.85 (s, 1H, aromatic), 8.28 (d, J=7 Hz, 1H, NH).

Mass Spectrum: (negative ion FAB) m/e 476 (P-1).

Elemental Analysis: Found C, 47.6; H, 4.4; N, 13.5; C$_{20}$H$_{20}$N$_5$O$_5$ClS. 1.5 H$_2$O requires C, 47.6; H, 4.6; N, 13.9%.

EXAMPLE 16

The process described in Example 12 was repeated except that di-tert-butyl N-[2-fluoro-4-(prop-2-ynyl)aminobenzoyl]-L-glutamate was used in place of diethyl N-[4-(prop-2-ynyl)aminobenzoyl]-L-glutamate. There was thus obtained N-[4-[N-(3-amino-4-chloroquinolin-6-ylmethyl)-N-(prop-2-ynyl)amino]-2-fluorobenzoyl]-L-glutamic acid (containing 1.5 equivalents of water), NMR Spectrum: (CD$_3$SOCD$_3$) 1.84-2.12 (m, 2H, CH$_2$), 2.32 (t, J=7 Hz, 2H, CH$_2$COOH), 3.25 (broad s, 1H, C≡CH), 4.3-4.45 (m, 3H, CH$_2$C≡C and NHCHCO), 4.87 (s, 2H, CH$_2$N), 6.65 (d of d's, J=1.5 and 14 Hz, 1H, aromatic), 6.71 (d of d's, J=1.5 and 9 Hz, 1H, aromatic), 7.37 (d of d's, J=1 and 5 Hz, aromatic), 7.55 (t, J=10 Hz, 1H, NH), 7.75-7.95 (m, 3H, aromatic), 8.54 (s, 1H, aromatic).

Mass Spectrum (negative ion FAB) m/e 511 (P-1).

Elemental Analysis: Found; C, 55.8; H, 4.5; N, 10.1; C$_{25}$H$_{22}$ClFN$_4$O$_5$. 1.5 H$_2$O requires C, 55.6; H, 4.7; N, 10.4%;

EXAMPLE 17

A mixture of 3-acetoxymethyl-6-bromomethyl-2-chloroquinoline (0.39 g), diethyl N-[4-(prop-2-ynyl)aminobenzoyl]-L-glutamate (0.43 g), 2,6-lutidine (0.193 g) and dry dimethylformamide (4 ml) was stirred and heated to 70° C. under an atmosphere of argon for 18 hours. The mixture was cooled to laboratory temperature, poured into water (20 ml) and extracted with ethyl acetate (3×20 ml). The combined extracts were evaporated and the crude product was purified by column chromatography on a silica gel column using increasingly polar mixtures of hexane and ethyl acetate as eluent to give a pale yellow foam (0.13 g).

A mixture of the product so obtained, ethanol (3 ml) and aqueous N sodium hydroxide solution (1 ml) was stirred at 22° C. for 2 hours. The mixture was evaporated and the residue was diluted with water (5 ml) and acidified to pH 3 by adding 2N hydrochloric acid solution. The precipitate was filtered off, washed with water (×3) and dried. There was thus obtained N-[4-[N-(2-chloro-3-hydroxymethylquinolin-6-ylmethyl)-N-(prop-2-ynyl)amino]benzoyl]-L-glutamic acid (containing 1.5 equivalents of water; 0.074 g), m.p. 134°-140° C.

NMR Spectrum: (CD$_3$SOCD$_3$) 1.8-2.2 (m, 2H, CH$_2$), 2.32 (t, J=7 Hz, 2H, CH$_2$COOH), 3.23 (s, 1H, C≡CH), 4.3-4.47 (m, 3H, NHCHCO and CH$_2$C≡C), 4.68 (s, 2H, CH$_2$OH), 5.63 (broad s, 1H, OH), 6.87 (d, J=8 Hz, 2H, aromatic), 7.68-7.81 (m, 3H, aromatic), 7.88-8.0 (m, 2H, aromatic), 8.23 (d, J=6 Hz, 1H, NH), 8.35 (s, 1H, aromatic).

Mass Spectrum: (negative ion FAB) m/e 508 (P-1).

Elemental Analysis: Found, C, 58.1; H, 4.9; N, 7.7; C$_{26}$H$_{24}$ClN$_3$O$_6$. 1.5 H$_2$O requires C, 58.2; H, 5.1; N, 7.8%.

The 3-acetoxy-2-chloro-6-methylquinoline used as a starting material for the preparation of 3-acetoxy-6-bromomethyl-2-chloroquinoline was prepared as follows:

A solution of sodium borohydride (0.25 g) in water (10 ml) was cooled to approximately 5° C. and added dropwise to a solution of 2-chloro-3-formyl-6-methylquinoline (1.38 g; prepared as described in Tet. Lett., 1979, 3111) in isopropanol (25 ml). The mixture was stirred at 5°-10° C. for 1 hour and then allowed to reach laboratory temperature. The mixture was partitioned between ethyl acetate and water. The aqueous layer was extracted with further portions of ethyl acetate and the combined organic extracts were dried (magnesium sulphate) and evaporated to leave a white solid (0.85 g).

A mixture of a portion (0.8 g) of the product so obtained, acetic anhydride (0.59 g), pyridine (0.46 g), N,N-dimethylaminopyridine (50 mg) and methylene chloride (20 ml) was stirred at 20° C. for 16 hours. The solution was washed with water (3×20 ml), dried and evaporated. The residue was purified by chromatography on a silica gel column using increasing polar mixtures of hexane and ethyl acetate as eluent. There was thus obtained 3-acetoxymethyl-2-chloro-6-methylquinoline (0.87 g).

EXAMPLE 18

The process described in Example 12 was repeated except that diethyl N-[5-methylaminothiazole-2-carbonyl]-L-glutamate was used in place of diethyl N-[4-(prop-2-ynyl)aminobenzoyl]-L-glutamate. There was thus obtained N-[5-[N-(3-amino-4-chloroquinolin-6-ylmethyl)-N-methylamino]thiazole-2-carbonyl]-L- glutamic acid (containing one equivalent of water), m.p. 140°-142° C., the structure of which was confirmed by proton magnetic resonance and mass spectroscopy and by elemental analysis.

EXAMPLE 19

A mixture of 6-bromomethyl-3,4-dichloroquinoline (0.5 g), diethyl N-[4-(prop-2-ynyl)aminobenzoyl]-L-glutamate (0.62 g), 2,6-lutidine (0.2 ml) and dry dimethylformamide (10 ml) was stirred and heated to 70° C. under an atmosphere of argon for 18 hours. The mixture was cooled and evaporated and the residue was purified by chromatography on a silica gel column using increasingly polar mixtures of ethyl acetate and methylene chloride as eluent. A mixture of the product so obtained (0.7 g), ethanol (10 ml) and aqueous N sodium hydroxide solution (8 ml) was stirred at 20° C. under argon for 2 hours. The ethanol was evaporated and the resulting aqueous solution was filtered and acidified to pH 3 by adding 2N hydrochloric acid solution. The precipitated solid was filtered off, washed with water and dried. There was thus obtained N-[4-[N-(3,4-dichloroquinolin-6-ylmethyl)-N-(prop-2-ynyl)amino]benzoyl]-L-glutamic acid (0.49 g, containing 1.5 equivalents of water), m.p. 116°-118° C.

NMR Spectrum: $(CD_3SOCD_3)$ 1.85-2.2 (m, 2H, $CH_2$), 2.33 (t, 2H, J=7 Hz, $CH_2COOH$), 3.24 (s, 1H, C≡CH), 4.3-4.45 (m, 3H, $CH_2\underline{N}$ and NH$\underline{CHCO}$), 4.97 (s, 2$\underline{H}$, $CH_2C≡CH$), 6.86 (d, 2H, J=8 Hz, aromatic), 7.74 (d, 2$\underline{H}$, J=8 Hz, aromatic), 7.83 (doublet of doublets, 1H, J=6.1 Hz, aromatic), 8.11 (d, 1H, J=6 Hz, aromatic), 8.14-8.27 (m, 2H, aromatic and CON$\underline{H}$), 8.96 (s, 1H, aromatic).

Elemental Analysis: Found C, 55.7; H, 4.2; N, 7.8; $C_{25}H_{21}Cl_2N_3O_5$. 1.5 $H_2O$ requires C, 55.5; H, 4.5; H, 7.8%.

3,4-Dichloro-6-methylquinoline, used as a starting material for the preparation of 6-bromomethyl-3,4-dichloroquinoline, was obtained as follows:

A mixture of 6-methyl-4-quinolone (20.0 g; J. Chem. Soc., 1948, 893), N-chlorosuccinimide (20.15 g) and benzoyl peroxide (0.2 g) was suspended in carbon tetrachloride (180 ml) and heated to reflux for 2 hours. The mixture was filtered and the solid was washed with methylene chloride and sucked dry to leave a white solid (18.5 g).

A mixture of this product (18.5 g), N,N-dimethylaniline (25.3 ml), phosphorus oxychloride (7.6 ml) and toluene (180 ml) was heated to 90° C. for 3 hours. The solution was cooled to 25° C., poured onto a mixture of ice and water (250 ml) and extracted with chloroform (4×150 ml). The combined extracts were evaporated and the residue was purified by chromatography on a silica gel column using methylene chloride as eluent. There was thus obtained 3,4-dichloro-6-methylquinoline (8.5 g).

EXAMPLE 20

The process described in Example 19 was repeated except that diethyl N-[5-methylaminothiazole-2-carbonyl]-L-glutamate was used in place of diethyl N-[4-(prop-2-ynyl)aminobenzoyl]-L-glutamate. There was thus obtained N-[5-[N-(3,4-dichloroquinolin-6-ylmethyl)-N-methylamino]thiazole-2-carbonyl]-L-glutamic acid (containing 1.5 equivalents of water), m.p. 115°-117° C., the structure of which was confirmed by proton magnetic resonance and mass spectroscopy and by elemental analysis.

EXAMPLE 21

The process described in Example 11 was repeated except that diethyl N-[5-methylaminothiazole-2-carbonyl]-L-glutamate was used in place of diethyl N-[4-(prop-2-ynyl)aminobenzoyl]-L-glutamate and 6-bromomethyl-3-(tert-butoxycarbonylamino)-2-chloroquinoline was used in place of 6-bromomethyl-2-(tert-butoxycarbonylamino)-4-chloroquinoline. There was thus obtained N-[5-[N-(3-amino-2-chloroquinolin-6-ylmethyl)-N-methylamino]thiazole-2-carbonyl]-L-glutamic acid (containing 1.25 equivalents of water), m.p. 124°-127° C., the structure of which was confirmed by proton magnetic resonance and mass spectroscopy and by elemental analysis.

3-(tert-Butoxycarbonylamino)-2-chloro-6-methylquinoline, used as a starting material for the preparation of 6-bromomethyl-3-(tert-butoxycarbonylamino)-2-chloroquinoline, was prepared as follows:

A solution of Jones reagent [prepared by mixing chromium trioxide (3.6 g), water (15 ml) and concentrated sulphuric acid (3.7 ml)] was added dropwise to a cooled solution (ice-bath) of 2-chloro-6-methylquinoline-3-carboxaldehyde (7.36 g; prepared as described in Tet. Lett., 1979, 3111) in acetone (150 ml). The mixture was stirred at 20° C. for 3 hours and then partitioned between ethyl acetate and water. The separated organic layer was extracted with aqueous N sodium hydroxide solution (3×35 ml) and the combined aqueous extracts were acidified to pH 3 by adding 2N aqueous hydrochloric acid solution. The prepcipitated solid was filtered off and dried to leave a white powder (7.6 g).

A mixture of this product (7.7 g), dimethylformamide (164 ml), tert-butanol (120 ml), diphenylphosphoryl azide (7.48 ml) and triethylamine (9.67 ml) was gradually heated to 100° C. and maintained at this temperature for 7 hours. After cooling to room temperature the volatile solvents were carefully evaporated and the residue was purified by chromatography on a silica gel column using increasingly polar mixtures of methylene chloride and petroleum ether (b.p. 60°-80° C.) as eluent. There was thus obtained 3-(tert-butoxycarbonylamino)-2-chloro-6-methylquinoline (6.87 g).

EXAMPLE 22

A mixture of 6-bromomethyl-3-(tert-butoxycarbonylamino)-2-chloroquinoline (0.5 g), di-tert-butyl N-[2-fluoro-4-(prop-2-ynyl)aminobenzoyl]-L-glutamate (0.58 g), 2,6-lutidine (0.16 ml) and dry dimethylformamide (10 ml) was heated to 70° C. for 14 hours under an atmosphere of argon. After being cooled to laboratory temperature the mixture was evaporated to dryness and the residue was purified by column chromatography on a silica gel column using increasingly polar mixtures of methylene chloride and ethyl acetate as eluent to give a white foam (0.4 g).

A mixture of this product (0.4 g) and trifluoroacetic acid (5 ml) was stirred at laboratory temperature for 1.5 hours. The trifluoroacetic acid was evaporated and the residue was dissolved in aqueous N sodium hydroxide solution. Acidification of the solution to pH 3 with aqueous N hydrochloric acid solution gave a pale cream precipitate which was filtered off and dried to leave, as an off-white powder (0.19 g), N-[4-[N-(3-amino-2-chloroquinolin-6-ylmethyl)-N-(prop-2-ynyl)amino]-2-fluorobenzoyl]-L-glutamic acid, (containing 1.25 equivalents of water), m.p. 107°-110° C.

NMR Spectrum: (CD₃SOCD₃) 1.8-2.2 (m, 2H, CH₂), 2.28 (t, J=7.3 Hz, 2H, CH₂COOH), 3.22 (broad s, 1H, C≡CH), 4.3-4.45 (m, 3H, NHCHO and CH₂C≡C), 4.77 (s, 2H, CH₂N), 5.75 (broad s, 2H, NH₂), 6.57-6.74 (m, 2H, aromatic), 7.27-7.35 (m, 2H, aromatic), 7.48-7.6 (m, 2H, aromatic), 7.69 (d, 1H, J=8.6 Hz, aromatic), 7.88 (doublet of doublets, 1H, J=5 and 8 Hz, CONH).

Mass Spectrum: (negative ion FAB) m/e 511 (P-1).

Elemental Analysis: Found C, 56.1; H, 4.6; N, 10.4; C₂₅H₂₂ClFN₄O₅. 1.25 H₂O requires C, 56.1; H, 4.6; N, 10.5%.

What we claim is:

1. A quinoline of the formula:

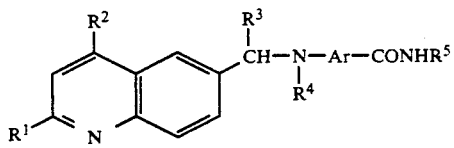

wherein each of R¹ and R², which may be the same or different, is hydrogen, halogeno, hydroxy, cyano, carbamoyl or amino; alkyl, alkoxy, alkylthio or alkanoylamino each of up to 4 carbon atoms; or each of R¹ and R², which may be the same or different, is alkyl of up to 3 carbon atoms which bears one hydroxy substituent or up to three halogeno substituents; provided that both R¹ and R² are not hydrogen;

wherein the quinoline ring either bears no further substituent or bears at the 3-, 5-, 7- or 8-position one further substituent selected from halogeno, amino, alkyl of up to 4 carbon atoms and alkyl of up to 3 carbon atoms which bears one hydroxy substituent;

wherein R³ is hydrogen or alkyl of up to 4 carbon atoms;

wherein R⁴ is hydrogen, alkyl, alkenyl or alkynyl each of up to 4 carbon atoms;

wherein Ar is phenylene which is unsubstituted or which bears one or two halogeno substituents, or Ar is thienylene or thiazolylene; and wherein R⁵ is such that R⁵—NH₂ is Glu or Val;

or a pharmaceutically-acceptable salt or ester thereof.

2. A quinoline as claimed in claim 1
wherein R¹ is hydrogen, halogeno, carbamoyl or amino; alkyl, alkoxy or alkanoylamino each of up to 4 carbon atoms; alkyl of up to 3 carbon atoms which bears one hydroxy substituent or up to three halogeno substituents;

wherein R² is hydrogen, halogeno, hydroxy or cyano; or alkyl, alkoxy or alkylthio each of up to 4 carbon atoms;

provided that both R¹ and R² are not hydrogen;

wherein the quinoline ring either bears no further substituent or bears at the 3-, 7- or 8-position one further substituent selected from halogeno, amino, alkyl of up to 4 carbon atoms and alkyl of up to 3 carbon atoms which bears one hydroxy substituent;

wherein R³ is hydrogen or alkyl of up to 4 carbon atoms;

wherein R⁴ is hydrogen, alkyl, alkenyl or alkynyl each of up to 4 carbon atoms;

wherein Ar is 1,4-phenylene which is unsubstituted or which bears one or two halogeno substituents, or Ar is thien-2,5-diyl or thiazol-2,5-diyl; and wherein R⁵ is such that R⁵—NH₂ is Glu or Val;

or a pharmaceutically-acceptable salt or ester thereof.

3. A quinoline as claimed in claim 1
wherein R¹ is hydrogen, chloro, amino, methyl, ethyl, methoxy or trifluoromethyl;

wherein R² is hydrogen, chloro, bromo, hydroxy, cyano, methyl or methoxy; provided that both R¹ and R² are not hydrogen;

wherein the quinoline ring either bears no further substituent or bears at the 3- or 7-position one further chloro, bromo or methyl substituent;

wherein R³ is hydrogen or methyl;

wherein R⁴ is hydrogen, methyl, ethyl, prop-2-enyl or prop-2-ynyl;

wherein Ar is 1,4-phenylene which is unsubstituted or which bears one or two fluoro substituents, or Ar is thien-2,5-diyl or thiazol-2,5-diyl (with the group —CONHR⁵ in the 2-position); and wherein R⁵ is such that R⁵—NH₂ is Glu or Val;

or a pharmaceutically-acceptable salt or ester thereof.

4. A quinoline as claimed in claim 1
wherein R¹ is hydrogen, halogeno, carbamoyl or amino; alkyl, alkoxy or alkanoylamino each of up to 4 carbon atoms; alkyl of up to 3 carbon atoms which bears one hydroxy substituent or up to three halogeno substituents;

wherein R² is hydrogen, halogeno, hydroxy or cyano; or alkyl, alkoxy or alkylthio each of up to 4 carbon atoms; provided that both R¹ and R² are not hydrogen;

wherein the quinoline ring either bears no further substituent or bears at the 3- or 7-position one further substituent selected from halogeno, amino, alkyl of up to 4 carbon atoms and alkyl of up to 3 carbon atoms which bears one hydroxy substituent;

wherein R³ is hydrogen or alkyl of up to 4 carbon atoms;

wherein R⁴ is hydrogen, alkyl, alkenyl or alkynyl each of up to 4 carbon atoms;

wherein Ar is 1,4-phenylene which is unsubstituted or which bears one halogeno substituent, or Ar is thien-2,5-diyl or thiazol-2,5-diyl; and wherein R⁵ is such that R⁵—NH₂ is Glu or Val;

or a pharmaceutically-acceptable salt or ester thereof.

5. A quinoline as claimed in claim 1
wherein R¹ is hydrogen, chloro, bromo, amino, methyl or trifluoromethyl;

wherein R² is hydrogen, chloro, bromo, methyl or methoxy; provided that both R¹ and R² are not hydrogen;

wherein the quinoline ring either bears no further substituent or bears a 8-fluoro, 3-chloro, 3-bromo, 3-amino, 3-methyl or 7-methyl substituent;

wherein R³ is hydrogen;

wherein R⁴ is hydrogen, methyl, ethyl, prop-2-enyl or prop-2-ynyl;

wherein Ar is 1,4-phenylene which is unsubstituted or which bears one fluoro substituent, or Ar is thien-2,5-diyl or thiazol-2,5-diyl (with the group —CONHR⁵ in the 2-position); and wherein R⁵ is such that R⁵—NH₂ is Glu or Val;

or a pharmaceutically-acceptable salt or ester thereof.

6. A quinoline as claimed in claim 1
wherein R¹ is hydrogen, chloro, amino or methyl;

wherein R² is hydrogen, chloro, bromo or methyl; provided that both R¹ and R² are not hydrogen;

wherein the quinoline ring either bears no further substituent or bears one further amino substituent at the 3-position;

wherein R³ is hydrogen;

wherein R⁴ is methyl, ethyl or prop-2-ynyl;

wherein Ar is 1,4-phenylene or 2-fluoro-1,4-phenylene (with the group —CONHR$^5$ in the 1-position); and wherein R$^5$ is such that R$^5$—NH$_2$ is Glu;

or a pharmaceutically-acceptable salt or ester thereof.

7. A quinoline selected from the group of compounds:

N-[4-[N-(2,4-dichloroquinolin-6-ylmethyl)-N-(prop-2-ynyl)amino]-2-fluorobenzoyl]-L-glutamic acid, N-[4-[N-(4-chloro-2-methylquinolin-6-ylmethyl)-N-(prop-2-ynyl)amino]-2-fluorobenzoyl]-L-glutamic acid, N-[4-[N-(4-bromo-2-methylquinolin-6-ylmethyl)-N-(prop-2-ynyl)amino]-2-fluorobenzoyl]-L-glutamic acid, N-[4-[N-(4-chloro-2-methylquinolin-6-ylmethyl)-N-ethylamino]-2-fluorobenzoyl]-L-glutamic acid, N-[4-[N-(2,4-dichloroquinolin-6-ylmethyl)-N-(prop-2-ynyl)amino]benzoyl]-L-glutamic acid, N-[4-[N-(4-chloro-2,7-dimethylquinolin-6-ylmethyl)-N-(prop-2-ynyl)amino]benzoyl]-L-glutamic acid, N-[4-[N-(4-chloro-2-trifluoromethylquinolin-6-ylmethyl)-N-(prop-2-ynyl)amino]benzoyl]-L-glutamic acid, N-[4-[N-(2-chloro-4-methoxyquinolin-6-ylmethyl)-N-(prop-2-ynyl)amino]benzoyl]-L-glutamic acid, N-[4-[N-(3-bromo-4-chloro-2-methylquinolin-6-ylmethyl)-N-(prop-2-ynyl)amino]benzoyl]-L-glutamic acid and N-[4-[N-(4-chloro-2-methylquinolin-6-ylmethyl)-N-(prop-2-ynyl)amino]benzoyl]-L-valine.

8. A quinoline selected from the group of compounds:

N-[5-[N-(3-amino-4-chloroquinolin-6-ylmethyl)-N-methylamino]thiazole-2-carbonyl]-L-glutamic acid, N-[4-[N-(2-amino-4-chloroquinolin-6-ylmethyl)-N-(prop-2-ynyl)amino]benzoyl]-L-glutamic acid, N-[4-[N-(2-amino-4-methylquinolin-6-ylmethyl)-N-(prop-2-ynyl)amino]benzoyl]-L-glutamic acid, N-[4-[N-(2-amino-4-chloroquinolin-6-ylmethyl)-N-(prop-2-ynyl)amino]-2-fluorobenzoyl]-L-glutamic acid, N-[4-N-(3-amino-2-chloroquinolin-6-ylmethyl)-N-(prop-2-ynyl)amino]-2-fluorobenzoyl]-L-glutamic acid, N-[4-[N-(3-amino-4-chloroquinolin-6-ylmethyl)-N-(prop-2-ynyl)amino]-2-fluorobenzoyl]-L-glutamic acid, N-[5-[N-(2-amino-4-chloroquinolin-6-ylmethyl)-N-methylamino]thiazole-2-carbonyl]-L-glutamic acid, N-[4-[N-(3-amino-4-chloroquinolin-6-ylmethyl)-N-(prop-2-ynyl)amino]benzoyl]-L-glutamic acid, N-[5-[N-(4-chloro-2-methylquinolin-6-ylmethyl)-N-methylamino]thiazole-2-carbonyl]-L-glutamic acid and N-[5-[N-(4-chloro-2-methylquinolin-6-ylmethyl)-N-methylamino]-2-thenoyl]-L-glutamic acid.

9. The compound N-[4-[N-(2,4-dichloroquinolin-6-ylmethyl)-N-(prop-2-ynyl)amino]-2-fluorobenzoyl]-L-glutamic acid.

10. A pharmaceutical composition for use in obtaining an anti-tumor effect which comprises an effective amount of a quinoline as claimed in claim 1, or a pharmaceutically-acceptable salt or ester thereof, in association with a pharmaceutically-acceptable diluent or carrier; the composition optionally containing one or more other anti-tumor substances selected from mitotic inhibitors, alkylating agents, other antimetabolites, intercalating antibiotics, enzymes, topoisomerase inhibitors and biological response modifiers.

* * * * *